United States Patent
Wang et al.

(10) Patent No.: US 10,405,750 B2
(45) Date of Patent: Sep. 10, 2019

(54) NONRADIATIVE VOLTAGE-SENSITIVE DYE FOR IMAGING NEURONAL ACTION POTENTIAL

(71) Applicant: Washington University, St. Louis, MO (US)

(72) Inventors: Lihong Wang, St. Louis, MO (US); Bin Rao, St. Louis, MO (US); Ruiying Zhang, St. Louis, MO (US)

(73) Assignee: Washington University, St. Louis, MO (US)

( * ) Notice: Subject to any disclaimer, the term of this patent is extended or adjusted under 35 U.S.C. 154(b) by 988 days.

(21) Appl. No.: 14/872,140

(22) Filed: Oct. 1, 2015

(65) Prior Publication Data
US 2016/0242651 A1    Aug. 25, 2016

Related U.S. Application Data

(60) Provisional application No. 62/057,824, filed on Sep. 30, 2014.

(51) Int. Cl.
| | | |
|---|---|---|
| A61B 5/00 | (2006.01) | |
| A61B 8/00 | (2006.01) | |
| A61B 8/13 | (2006.01) | |
| A61M 5/00 | (2006.01) | |
| A61B 8/08 | (2006.01) | |

(52) U.S. Cl.
CPC .......... *A61B 5/0073* (2013.01); *A61B 5/0048* (2013.01); *A61B 5/0095* (2013.01); *A61B 5/4058* (2013.01); *A61B 5/4848* (2013.01); *A61B 5/6868* (2013.01); *A61B 8/0808* (2013.01); *A61B 8/13* (2013.01); *A61B 8/4494* (2013.01); *A61M 5/007* (2013.01); *A61B 2503/40* (2013.01); *A61B 2503/42* (2013.01)

(58) Field of Classification Search
None
See application file for complete search history.

(56) References Cited

U.S. PATENT DOCUMENTS

| | | | |
|---|---|---|---|
| 2011/0201914 A1* | 8/2011 | Wang | A61B 5/0059 600/407 |
| 2012/0289869 A1 | 11/2012 | Tyler | |

FOREIGN PATENT DOCUMENTS

WO    2008016581 A2    2/2008

OTHER PUBLICATIONS

"Photoacoustic Tomography: In Vivo Imaging from Organelles to Organs" by L.V. Wang et al. Science. vol. 335. pp. 1458-1462. 2012.*
"Contrast-enhanced photoacoustic imaging of live lobster nerve cord" by R.S. Witte et al. Photons Plus Ultrasound: Imaging and Sensing 2007: The Eighth Conference on Biomedical Thermoacoustics. Proc. Of SPIE vol. 6437. pp. 1-10. 2007.*

(Continued)

*Primary Examiner* — Tse W Chen
*Assistant Examiner* — Jason M Ip
(74) *Attorney, Agent, or Firm* — Armstrong Teasdale LLP

(57) ABSTRACT

A method for fast high-resolution deep photoacoustic tomography of action potentials in brains is provided herein. The method may utilize a high-speed, high-spatial-resolution, deep-penetration photoacoustic computed tomography (PACT) system for real-time imaging of action potentials.

16 Claims, 16 Drawing Sheets
(15 of 16 Drawing Sheet(s) Filed in Color)

(56) References Cited

OTHER PUBLICATIONS

"Visualizing the Cortical Representation of Whisker Touch: Voltage-sensitive Dye Imaging in Freely Moving Mice" by I. Ferezou et al. Neuron. 50, pp. 617-629, 2006.*
Fromherz, P. et al, "ANNINE-6plus, a voltage-sensitive dye with good solubility, strong membrane binding and high sensitivity," European Biophysics Journal, 37(4): 509-514 (2008).
Jo, J. et al., "Photoacoustic detection of functional responses in the motor cortex of awake behaving monkey during forelimb movement," Journal of Biomedical Optics, 17(11)=110503-1 to 110503-3 (2012).

* cited by examiner

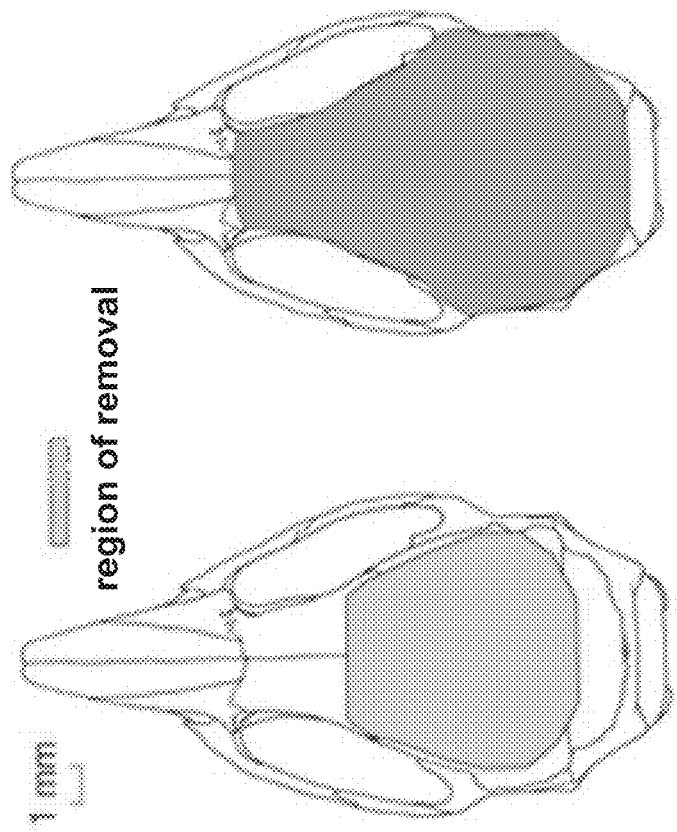
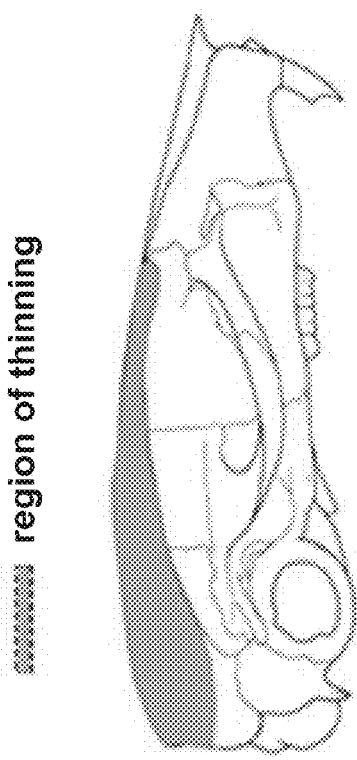
FIG. 8A
FIG. 8B

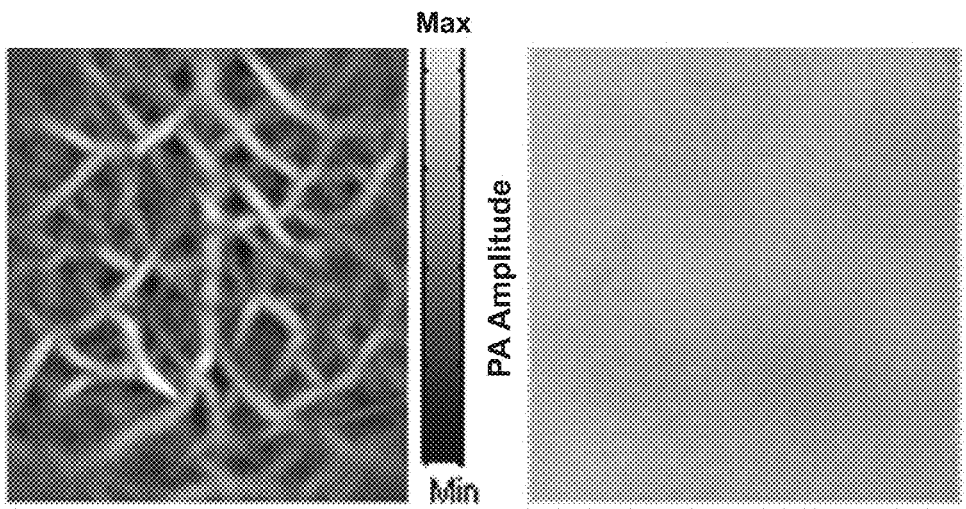
FIG. 9A  FIG. 9B
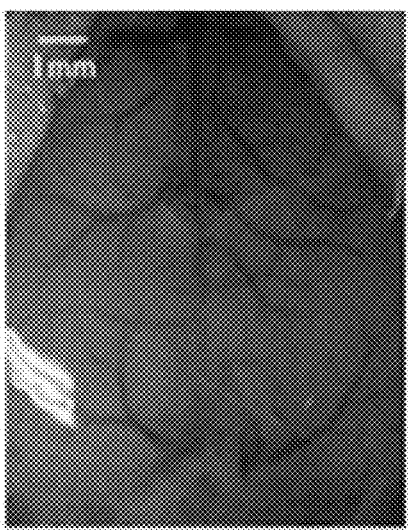 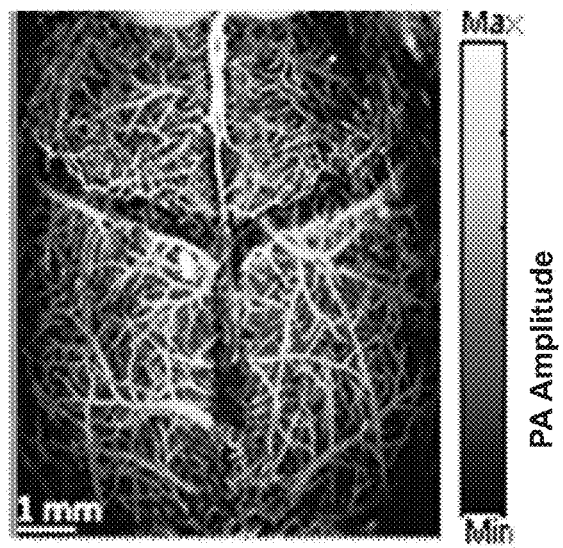
FIG. 9C  FIG. 9D

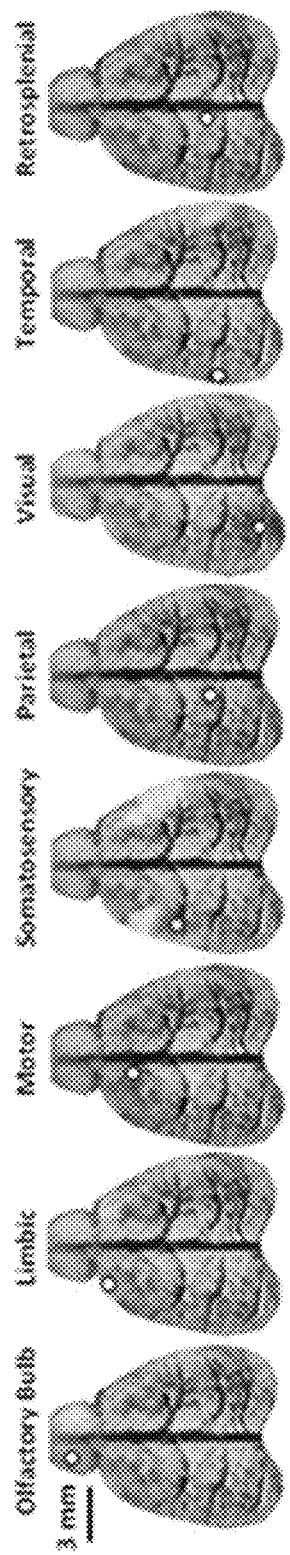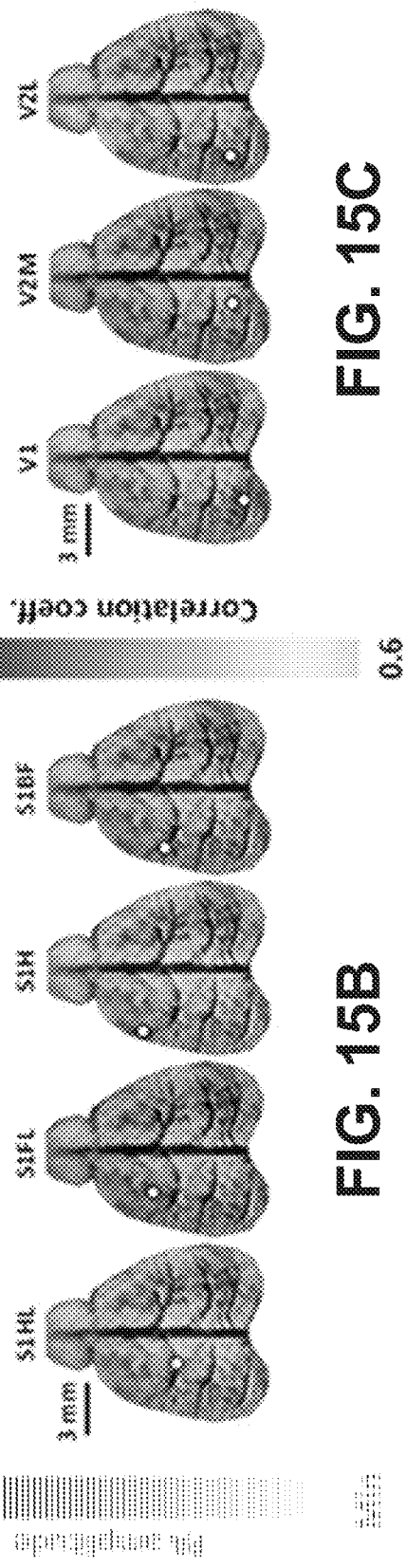
FIG. 15A
FIG. 15B
FIG. 15C

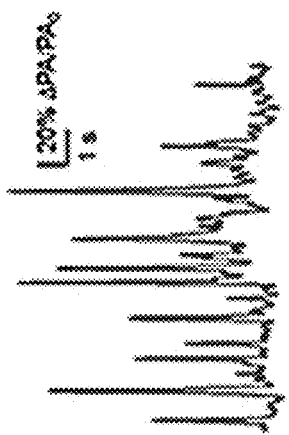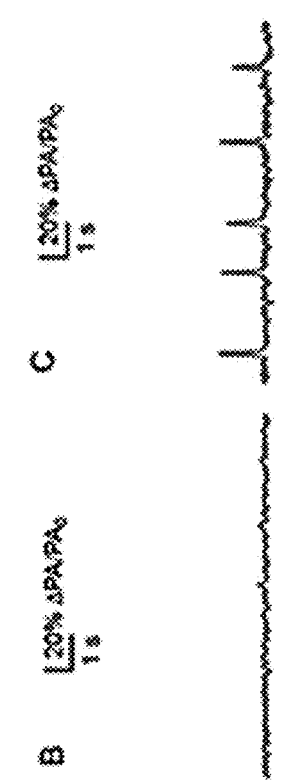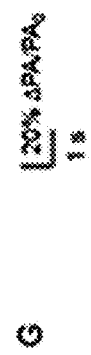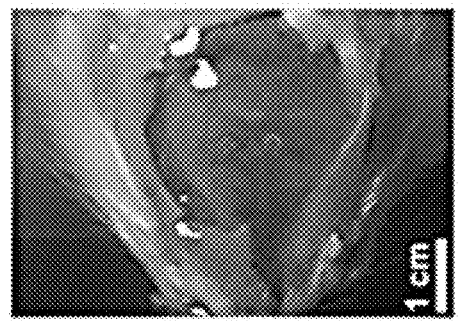

NONRADIATIVE VOLTAGE-SENSITIVE DYE FOR IMAGING NEURONAL ACTION POTENTIAL

CROSS-REFERENCE TO RELATED APPLICATIONS

This application claims priority to U.S. Provisional Patent Application No. 62/057,824 filed on Sep. 30, 2014, which is hereby incorporated by reference in its entirety.

STATEMENT REGARDING FEDERALLY SPONSORED RESEARCH & DEVELOPMENT

This invention was made with government support under grants U01 NS090579 awarded by the U.S. National Institutes of Health. The U.S. government may have certain rights in this invention.

COLOR DRAWINGS

The patent or application file contains at least one drawing executed in color. Copies of this patent or patent application publication with color drawing(s) will be provided by the Office upon request and payment of the necessary fee.

FIELD OF THE INVENTION

The present invention relates to non-radiative voltage-sensitive dyes that not only have significantly higher signal variation ($\Delta I/I$) than fluorescence technologies, but also enable deep brain action potential recording using photoacoustic imaging methods such as photoacoustic microscopy and photoacoustic tomography.

BACKGROUND

Visualizing and quantifying the electrical activity of brains, in particular at the cellular level, has facilitated the progress of research entailing the understanding and treatment of neurological diseases such as Alzheimer's and Parkinson's. Although electrode-based methods are valuable and traditional tools for measuring the membrane potential of single neurons and MRI imaging. These methods have provided scientists with knowledge of large-scale brain activity over time scales of seconds to minutes, but no method to date has elucidated the connection between microscopic interactions at the neuronal level and macroscopic structures that perform complex computations. Moreover, electrode-based methods suffer from their mechanically invasive nature and inability to target genetically labeled subpopulations, or to monitor subcellular compartments. Besides limited by its temporal resolution, MRI also requires a costly magnetic field to achieve high spatial resolution.

By comparison, optical imaging techniques are well-positioned for measuring membrane potential noninvasively on multiple spatial and temporal scales, for both subcellular compartments and neuronal microcircuits. Deep optical imaging at high resolution inside biological tissue is challenging to implement because of the strong scattering characteristics of biological tissues. One optical imaging technique, multiphoton microscopy (MPM) has extended the imaging depth of high-resolution optical imaging and has enabled visualization of neuronal activity in the brains of small animals, but light scattering by biological tissues limits the penetration depth of MPM to about 1 mm.

A need exists to measure membrane potential non-invasively using high resolution optical imaging methods capable of reaching deep tissues within the brain of an animal subject.

SUMMARY

Provided herein is a method of performing photoacoustic tomography of at least one electrically-active cell of a subject, the method including contacting the at least one electrically-active cell within a target area with a voltage-responsive dye; illuminating the target area with a light pulse; detecting at least one photoacoustic signal produced by the voltage-responsive dye; comparing the time-of-arrival of the at least one photoacoustic to determine the position of the at least one electrically-active cell; and comparing at least one characteristic of the photoacoustic signal to a calibration rule to determine a voltage of the at least one voltage-responsive cell, wherein the at least one characteristic is chosen from: amplitude, duration, temporal profile, frequency, and any combination thereof.

The light pulse may include a pulse wavelength corresponding to a maximum absorption wavelength of the voltage-responsive dye. The pulse wavelength may range from about 400 nm to about 920 nm. The light pulse may further include a pulse frequency of at least about 1 kHz. The target area may be illuminated using at least one illumination scheme chosen from: directing the light pulse through a diffuser to produce planar top Illumination; directing the light pulse through at least two optic fibers and through one or more diffusers to produce illumination from two or more directions; directing the light pulse through a side-firing optical fiber into an external cavity of a subject chosen from a mouth, a nasal cavity, an ear canal, a gastrointestinal tract, a urethra, or a vagina; directing the light pulse through an optical fiber implanted within the subject; and any combination thereof.

The at least one electrically-active cell may be chosen from at least one of: a brain neuron, a spinal neuron, a peripheral neuron, a sensory neuron, a voluntary muscle cell, a smooth muscle cell, a cardiac muscle cell, and any combination thereof. The at least one photoacoustic signal may be detected at a depth up to about 50 mm. The at least one photoacoustic signal may be detected within a detection time of less than about 5 µs. The position of the at least one electrically-active cell may be detected with a spatial resolution of less than about 100 µm. The position of the at least one electrically-active cell may be detected with a spatial resolution of about 25 µm.

The voltage-sensitive dye may be contacted with the at least one electrically active cell within the target area using a contact method chosen from: intravenous injection; intramuscular injection; intraventricular injection; spinal tap; craniotomy with direct contact of dye to cortical surface of brain; or introduction of dye into a cell preparation containing the at least one electrically active cell. voltage-sensitive dye The voltage-responsive dye may be selected from: a merocyanine-rhodanine dye including NK 2761; an aminonaphthylethenylpyridinium dye including Di-4-ANEPPS, di-8-ANEPPS, Di-2-ANEPEQ, Di-8-ANEPPQ and Di-12-ANEPPQ; a dialkylaminophenylpolyenylpyridinium dye including RH 160, RH 237, RH 414, RH 421, and RH 795; an oxonol dye including RH 155, RH 482, RH 1691, RH 1692, and RH 1838; and dipicrylamine (DPA).

The method may further include electrically stimulating a region within the target area to induce an electrical response within the target region. The hippocampus of a brain may be the target region and a perforant pathway may be electrically stimulated to induce a response within the hippocampus. The method may further include stimulating a sensory neuron to induce a response within the target region comprising a brain. The sensory neuron may be chosen from a visual neuron, an olfactory neuron, an auditory neuron, a taste neuron, a pressure-sensitive neuron, and a temperature sensitive neuron. The method of the target area may include a brain, and a cognitive task is used to induce electrical activity within the target area.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following figures illustrate various aspects of the disclosure.

FIG. 8A is an illustration of a craniectomy according to one aspect. FIG. 8B is an illustration of a skull thinning procedure according to one aspect.

FIG. 9A is an in vivo PACT image of mouse cortical vessels acquired non-invasively at 532 nm wavelength. FIG. 9B is a photograph of the same brain cortex with an intact scalp. FIG. 9C is a photograph of the brain cortex shown in FIG. 9B exposed by a craniectomy. FIG. 9D is an in vivo OR-PAM image of mouse brain vessels acquired through an intact skull.

FIG. 15A is a series of correlation maps of the eight main functional regions of a live mouse brain acquired noninvasively by PAT according to one aspect; the functional regions included are: olfactory bulb, limbic, motor, somatosensory, parietal, visual, temporal, and retrosplenial. FIG. 15B is a series of correlation maps of the four subregions of the somatosensory cortex of a live mouse brain acquired noninvasively by PAT according to one aspect: S1HL, S1FL, S1H, and S1BF. FIG. 15C is a series of correlation maps of the three subregions of the visual cortex of a live mouse brain (V1, V2M, and V2L) acquired noninvasively by PAT according to one aspect. White circles indicate the seed regions. S1HL, primary somatosensory cortex—hindlimb region; S1FL, primary somatosensory—forelimb region; S1H, primary somatosensory—head region; S1BF, primary somatosensory—barrel field. V1, primary visual cortex; V2M, secondary visual cortex—medial region; V2L, secondary visual cortex—lateral region.

FIG. 18A is a photograph of an open skull window with a superimposed green cross representing the location for M-mode PA imaging according to an aspect. FIG. 18B is a graph showing the baseline fractional PA signal changes ($\Delta PA/PA_0$) acquired before DPA infusion. FIG. 18C is a graph showing the fractional PA signal changes ($\Delta PA/PA_0$) acquired after DPA infusion. FIG. 18D is a graph showing the baseline fractional PA signal changes ($\Delta PA/PA_0$)

acquired during 4-AP-induced seizures. FIG. 18E is a graph showing the fractional PA signal changes ($\Delta PA/PA_0$) acquired immediately after a 5% isoflurane challenge. FIG. 18F is a graph showing the fractional PA signal changes ($\Delta PA/PA_0$) acquired 5 minutes after the 5% isoflurane challenge. FIG. 18G is a graph showing the fractional PA signal changes ($\Delta PA/PA_0$) acquired 30 minutes after the 5% isoflurane challenge.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, a method of determining changes in a membrane voltage of at least one electrically active cell using photoacoustic imaging in conjunction with a voltage-sensitive dye composition. In one aspect, the method may determine changes in a membrane voltage of an electrically active cell in vitro using a photoacoustic microscopy system. In another aspect, the method may determine changes in a membrane voltage of electrically active cells in vivo using a photoacoustic tomography (PAT) system.

Figure 19:
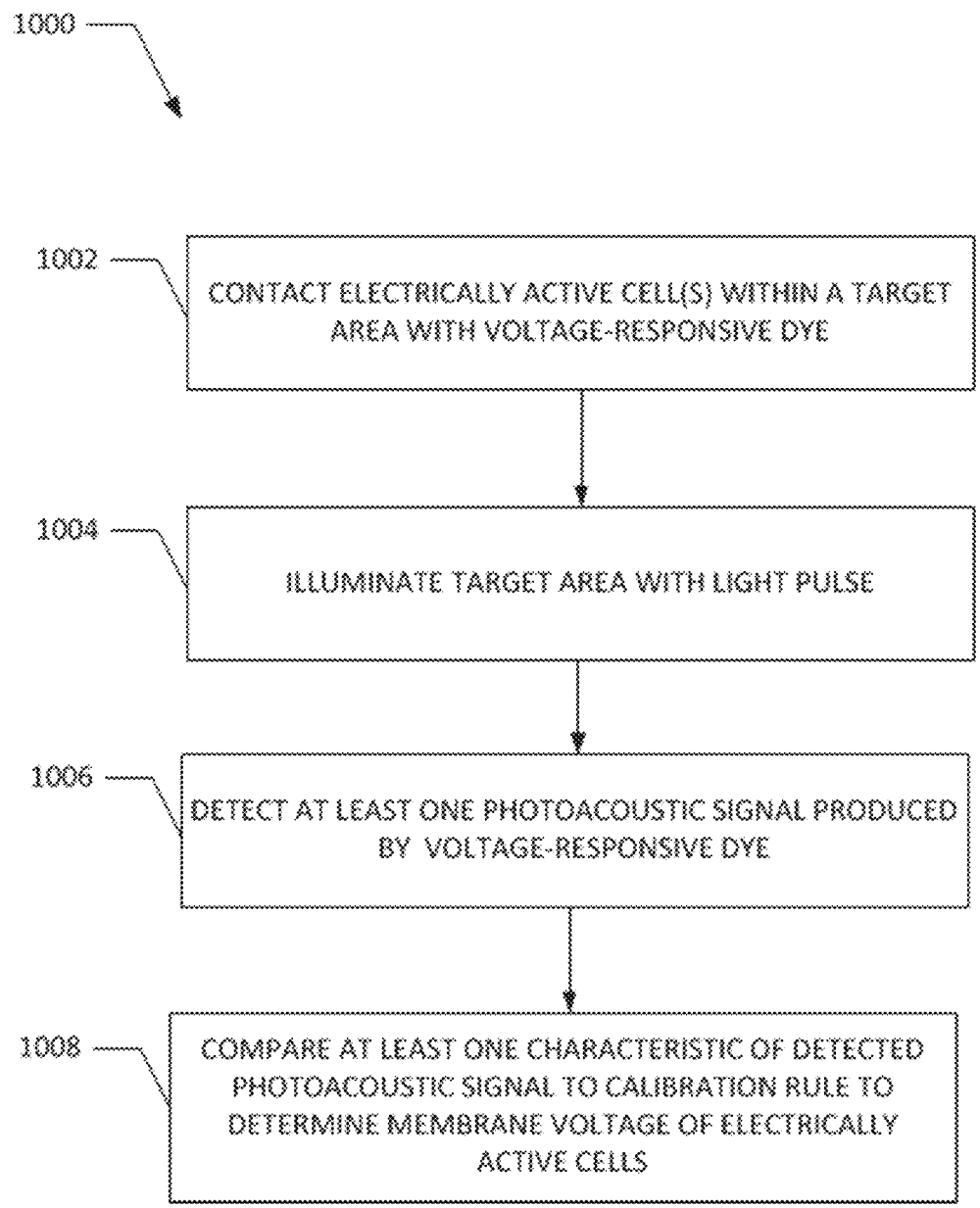
FIG. 19 is a flow chart illustrating the steps of a method 1000 for determining changes in a membrane voltage of an electrically active cell using photoacoustic imaging in accordance with one aspect.

FIG. 19 is a flow chart summarizing the steps of a method 1000 in one aspect. In one aspect, the method includes contacting the at least one electrically active cell with a voltage-responsive dye at step 1002. In various aspects, the at least one electrically active cell includes, but is not limited to: a brain neuron, a spinal neuron, a peripheral neuron, a sensory neuron, a voluntary muscle cell, a smooth muscle cell, a cardiac muscle cell, and any combination thereof. In one aspect, the at least one electrically active cell is positioned within a cell culture and the method 1000 is performed in vitro. In another aspect, the at least one electrically active cell is positioned within a living tissue of an animal including, but not limited to a nerve, a spinal cord, and an animal brain and/or a substructure of an animal brain including, but not limited to a hippocampus, a brain stem, a cortex, any other brain structure, without limitation.

Referring again to FIG. 19, the voltage responsive dye may be contacted with the at least one electrically active cell using any known method including, but not limited to: intravenous injection; intramuscular injection; intraventricular injection; spinal tap; craniotomy with direct contact of dye to cortical surface of brain; or introduction of dye into a cell preparation containing the at least one electrically active cell.

Referring again to FIG. 19, the target area containing the voltage-sensitive dye and at least one electrically-active cell is illuminated with a light pulse produced by a light source of the PA imaging device at step 1004. In one aspect, the characteristics of the light pulse including, but not limited to, wavelength and pulse fluence, are selected to fall within a region of relatively high PA signal response of the voltage-sensitive dye compared to surrounding tissues including, but not limited to, blood cells such as red blood cells. In one aspect, the light pulse is produced at a wavelength within the red or NIR window to further facilitate penetration into living tissues due to the relatively low scattering of red or NIR light pulses within the living tissues.

Referring again to FIG. 19, photoacoustic signals produced by the voltage-sensitive dye within the target area is detected by an ultrasound transducer of the photoacoustic imaging device at step 1006. At least one characteristic of the detected photoacoustic signal is compared to a calibration rule at step 1008 to determine a membrane voltage of the at least one electrically active cell within the target area. By way of non-limiting example, the calibration rule determines the membrane voltage based on the amplitude of the photoacoustic signal, as described herein.

PA computed tomography (PACT) is a major implementation of PAT that uses the state-of-the-art ultrasonic array detectors. It can provide fast data acquisition, cellular resolution, and deep penetration beyond the optical diffusion limit. Non-invasive, label-free, and functional PACT of the brains of small animals has been demonstrated by accurately mapping brain lesions and cerebral hemodynamics.

In an aspect, a PACT system may be customized for neuroimaging, which may allow fast acquisition of high resolution images (2 kHz frame rate and 25 µm spatial resolution). In an aspect, voltage-sensitive dyes may be used for photoacoustic imaging in cell cultures and then in mouse brains in vivo. This imaging modality may enable the recording of dynamic neuronal activity of large numbers of neurons within deep brain tissues. 25-µm resolution of the PACT system can be further improved through multiscale imaging according to the depth of interest. For example, for 3-mm depth, a 7.5-µm resolution is expected to be attainable; for 1-mm depth, submicron resolutions have been shown.

Voltage-sensitive probes may be screened for photoacoustic imaging in cell culture preparations and optimize detection parameters. To minimize optical attenuation in tissue, various voltage-sensitive dyes for photoacoustic imaging are screened using light pulses in the red or NIR spectral window in one aspect. In another aspect, a voltage clamp system with a transmission-mode optical-resolution photoacoustic microscope (OR-PAM) to image the voltage-sensitive dyes and optimize the laser wavelength and pulse energy may be used. In an aspect, the cell culture preparation is a HEK-293 cell culture in which the membrane action potential of the HEK-293 cells are electrically excited and measured by both OR-PAM and voltage clamp. In various aspects, the effects of the optical excitation wavelength and optical pulse energy may be varied to maximize the sensitivity of the candidate voltage-sensitive dye, i.e., the photoacoustic signal change per 100 mV of membrane potential change.

Non-limiting examples of suitable voltage-sensitive dyes include: merocyanine-rhodanine dyes including NK 2761; minonaphthylethenylpyridinium dyes including Di-4-ANEPPS, di-8-ANEPPS, Di-2-ANEPEQ, Di-8-ANEPPQ and Di-12-ANEPPQ; dialkylaminophenylpolyenylpyridinium dyes including RH 160, RH 237, RH 414, RH 421, and RH 795; oxonol dyes including RH 155, RH 482, RH 1691, RH 1692, and RH 1838; and dipicrylamine (DPA). In an exemplary aspect, the voltage-sensitive dye contacted with the at least one electrically active cell is DPA. In one aspect, DPA has a significantly higher PA sensitivity than related fluorescent dyes.

In various aspects, the detection time of the PA imaging device is on the order of several µs, which is much faster than the time scale of action potential signals. Thus, a voltage-sensitive dye used as a PA probe is limited only by how fast the molecules of voltage-sensitive dye including, but not limited to DPA migrate between the inner leaflet and outer leaflet of the cell membrane. IN one aspect, DPA dye is characterized by a faster migration compared to other DPA-based fluorescent hybrid dyes such as DiO/DPA. In other aspects, DPA has additional advantages in its simplicity, lower toxicity, and easier delivery compared to other voltage-sensitive fluorescent hybrid dyes.

A fast, high-resolution, deep-penetration PACT system may be developed. We propose to develop a new photoacoustic neuroimaging system based on a high-frequency full-ring transducer array and a high pulse repetition rate laser as well as a linear array. The new ring-shaped system will achieve a frame rate of 2 kHz and an in-plane spatial resolution of 25 µm, which are 3200 times faster and three times finer, respectively, than those of our prototype full-ring array system. A high-frequency linear array will also be used to provide coverage from the top of the brain and hence improve the depth resolution. Such a high frame rate and spatial resolution will allow us to track the action potentials of the entire mouse brain.

The photoacoustic neuroimaging system, for the first time, may allow high-speed and high-resolution imaging of neuroactivity throughout the entire mouse brain. The system may consist of a multichannel ultrasound acquisition system, a high-frequency full-ring transducer array, and a high-repetition-rate laser. The neural activity may be monitored photoacoustically through a voltage-sensitive dye. In an aspect, a frame rate of about 2 kHz and a spatial resolution of about 25 µm may be acquired. Such a high frame rate and spatial resolution may allow tracking of the action potentials of the mouse brain in real time.

PACT may be used to image action potentials in mouse brains in vivo. We will apply the voltage-sensitive photoacoustic imaging probe at the optimized wavelength to in vivo mouse brain imaging with our proposed PACT system. First, the voltage-sensitive photoacoustic imaging probe will be pressure-injected into the mouse brain. Then action potential changes in neuronal networks induced by electrical stimulations will be imaged by PACT. The photoacoustic signal changes from the stimulated areas of the mouse brains will be imaged and quantified before and after the electrical stimulation. To demonstrate the deep penetration capability of the proposed method, neuronal networks at various depths will be imaged. Microelectrodes will be used to measure the local field potential change within the stimulated areas, which will be compared with the local photoacoustic signal change as a validation of the proposed technology.

In addition to the proposed skull thinning or removal, alternative methods including, but not limited to, skull softening using chemicals significantly improves acoustic transmission through skull. We have also made considerable progress in correcting skull aberration using iterative image reconstruction that incorporates the effect of the skull. It has already been scaled up for ex vivo monkey and adult human imaging through intact skull. We are currently pushing in vivo human brain imaging of hemoglobin contrast.

It is widely accepted that DPA can be used as a cytoplasmic membrane potential sensor because the membrane location of DPA changes as a function of the polarity and magnitude of membrane potential. Used in combination with another fluorescent dye such as DiO (FRET donor), a membrane potential-dependent FRET signal can be generated. Our previous cell culture experiments demonstrated the membrane potential-dependent optical absorption of DPA, which was further confirmed by our recent in vivo animal brain imaging results (see below). The direct photoacoustic probing of DPA also showed a much greater signal change than FRET probing.

In one aspect, in vivo imaging is performed in mouse brains to examine neural activity using pharmacological manipulations. After creating an open skull window, a cortical region was located (identified by the cross in FIG. 18A) with less dense vasculature for M-mode photoacoustic imaging. In the absence of DPA dye, baseline M-mode imaging shows no activity (FIG. 18B). Shortly after topically applying DPA dye, we recorded intermittent low-amplitude PA signal consistent with isolated spontaneous neural activity (FIG. 18C). After injection of 4-am inopyridine (4-AP, a potassium channel agonist), the mice manifested signs of convulsions. Photoacoustic imaging during this period demonstrated large-amplitude high-frequency waveforms consistent with epileptiform discharges (FIG. 18D). After administration of 5% isoflurane, the waveform evolved to rhythmic bursts of very-high amplitude photoacoustic signals (FIG. 18E, note the amplification of the vertical scale), which attenuated over time (FIG. 18F). Prolonged exposure to isoflurane (30 minutes) resulted in the suppression of photoacoustic signal change (FIG. 18G), and death of the mouse shortly thereafter. These robust photoacoustic recordings during various pharmacological manipulations in the living mouse show great promise, but will require validation with simultaneous microelectrode recordings of local field potentials, as proposed in the grant application.

Conventional optical imaging modalities for the imaging of action potential, such as two photon and confocal microscopy, have limited imaging depth and spatial resolution for in vivo mouse brain imaging. However, photoacoustic imaging can break this barrier by detecting action potential signals via ultrasound waves, which attenuate far less than light. The in vivo small animal brain imaging with the improved PACT system offers several advantages. It has submillisecond temporal resolution, micron-scale spatial resolution, and multi-mm deep penetration into the mouse brain. Moreover, the voltage-sensitive photoacoustic imaging dye, which yields a ~200% PA signal change in cell culture experiments, may provide high sensitivity to action potentials in mouse brains. Fast and high-resolution imaging of the mouse brain at depths may be achieved which have never been explored before by other optical imaging techniques.

Several strategies will be used to differentiate PA signals originating from blood vs. DPA. First, the absorption spectral differences between DPA dye and hemoglobin will be exploited. Second, the temporal differences between DPA vs. vascular signals can be exploited to distinguish the two signals. Simple time-frequency analysis could separate high-frequency action potential spikes (see FIG. 18B and FIG. 18C and FIG. 18D and FIG. 18E and FIG. 18F and FIG. 18G.) from slower hemodynamics changes, and further suppress static or slowly varying background signals due to heart beating or breathing.

EXAMPLES

Example 1: Screen Voltage-Sensitive Photoacoustic Imaging Probes in Human Embryonic Kidney (HEK) 293 Cell Culture Preparations and Optimize Detection Parameters HEK 293 cells stained with the hybrid DiO/DPA dye were imaged under different resting potentials. HEK 293 cell membrane resting potential was changed by changing the environmental potassium ion concentration. DPA dye alone may provide voltage-sensitive photoacoustic contrast. HEK 293 cells stained with DPA alone were imaged under different resting potentials. The results demonstrated a new voltage-sensitive photoacoustic imaging probe. An ~200% PA signal change was observed with an ~68 mV membrane resting potential change induced by a potassium (K+) concentration change in the extracellular space. Additional dyes may be screened for an optimal optical excitation wavelength in the deep-penetration optical window (red or NIR), the results may be quantified using the voltage clamp technique as the gold standard, and optical pulse energy may be optimized for the detection of voltage-sensitive photoacoustic imaging probes. The selected dyes and optimized parameters may be applied in the in vivo mouse brain imaging experiment.

Example 2: Our Preliminary Results Demonstrated PA Contrast in Imaging the Cell Membrane Action Potential with a Hybrid Dye Experiments with a human embryonic kidney (HEK) 293 cell culture preparation and a transmission mode optical resolution photoacoustic microscope were conducted. HEK293 cells were stained with DiO/DPA hybrid dye before replacing the extracellular space with Dulbecco's phosphate buffered saline. Stained cells were imaged in DPBS to acquire a baseline image, with the baseline cell membrane resting potential denoted by $V_{m0}$. The cell membrane resting potential was varied by changing the cells' external environmental potassium ($K^+$) concentration.

Figure 1:
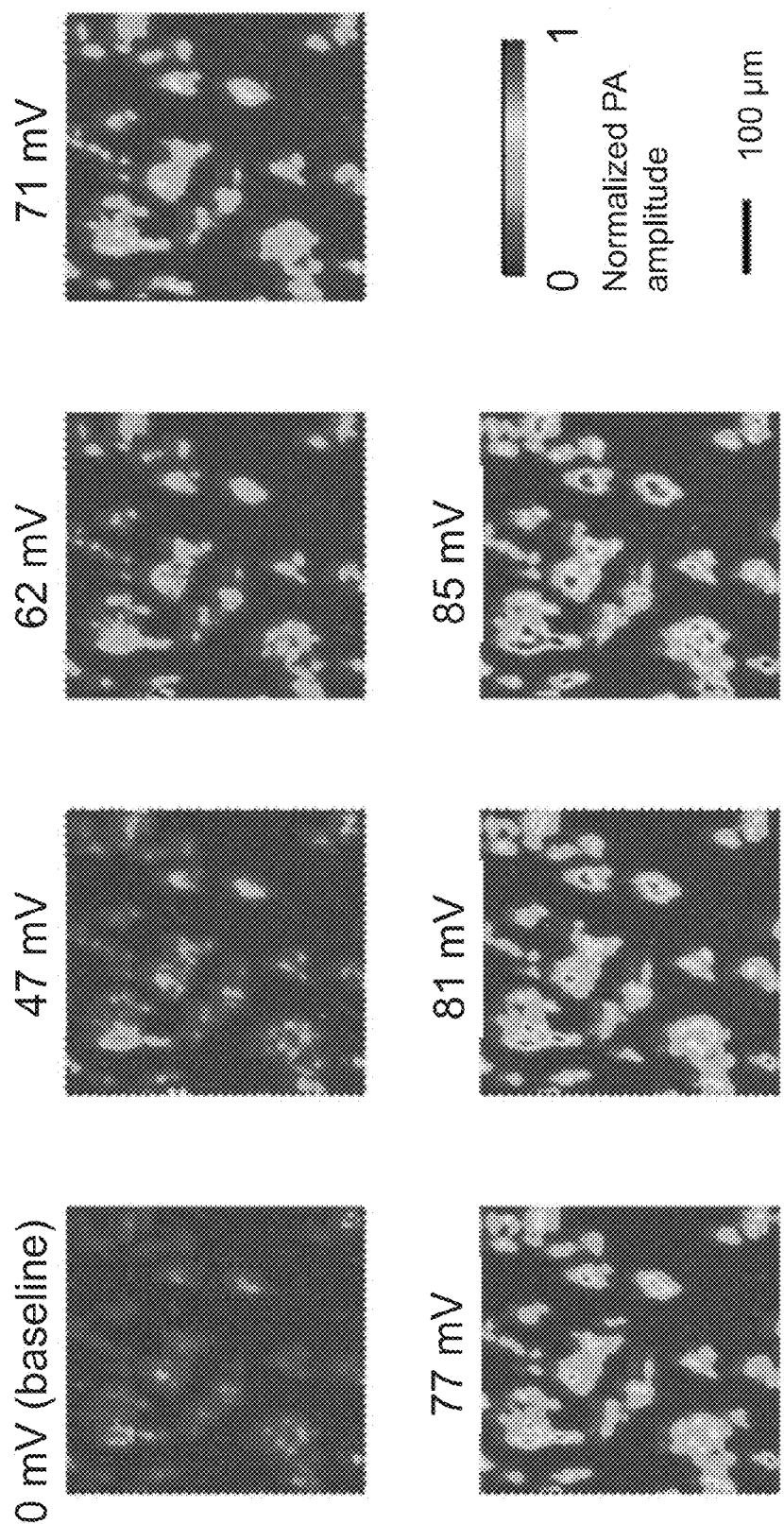
FIG. 1 is a series of PA images of HEK 293 cells stained with DiO/DPA voltage-sensitive dye at different relative membrane resting potentials: 0 mV (baseline), 47 mV, 62 mV, 71 mV, 77 mV, 81 mV, and 85 mV. The DPA concentration is 5 µM.
Figures 2A, 2B:
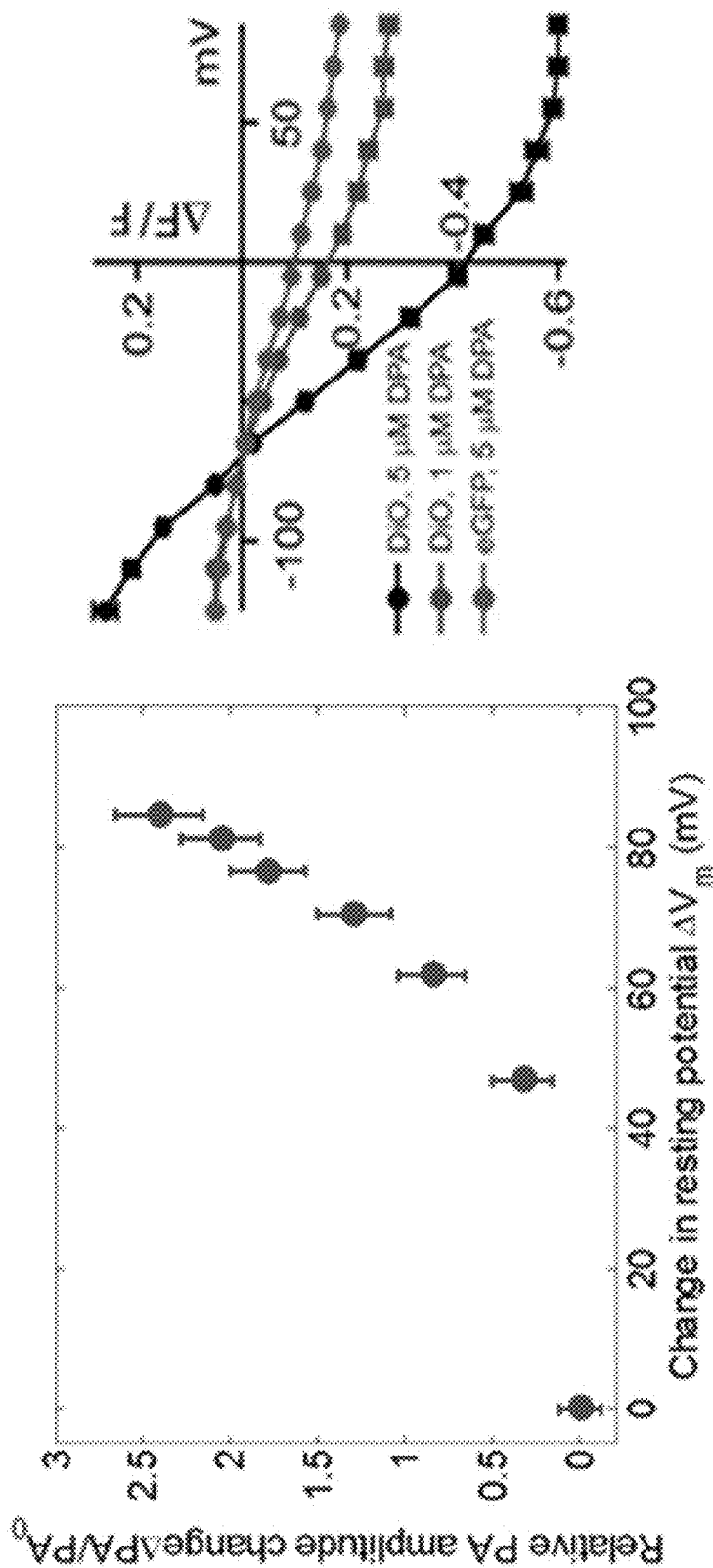
FIG. 2A is a graph of PA amplitude changes measured at a range different relative resting potentials relative to a baseline PA amplitude $PA_0$ measured at a baseline resting potential $V_{m0}$.
FIG. 2B is a graph of the changes in fluorescence of DiO/DPA FRET pairs in response to voltage steps.

Using the Nernst equation, the change in resting potential relative to the baseline was estimated. Cell images were acquired with optical-resolution photoacoustic microscopy (OR-PAM) as the cell membranes underwent a series of resting potential changes relative to the baseline (FIG. 1 is a series of). FIG. 2(*a*) shows the corresponding relative PA amplitude changes of HEK 293 cells under different relative resting potentials, calculated from chosen areas of cells denoted by the red dashed squares in FIG. 1. The error bars represent standard deviations (SD) of the PA amplitudes. The PA changes relative to the baseline are as high as 250% (2.5×). FIG. 2A shows the fluorescence changes of DiO/DPA FRET pairs of HEK 293 cells in response to voltage steps, which is less than 60%. Therefore, the relative PA changes are >4× greater than the relative fluorescence changes.

Both the DiO and DPA dyes absorb pulsed excitation laser illumination at 488 nm. DiO dye is attached to the cell membrane, while the DPA molecules migrate between the inner leaflet and outer leaflet of the cell membrane. DPA molecules close to the DiO molecules will quench the fluorescence signal of DiO. The quenched fluorescence energy will be transformed into heat and produce a photoacoustic signal. We conducted our second preliminary study by imaging HEK 293 cells stained with DPA alone.

Figure 3:
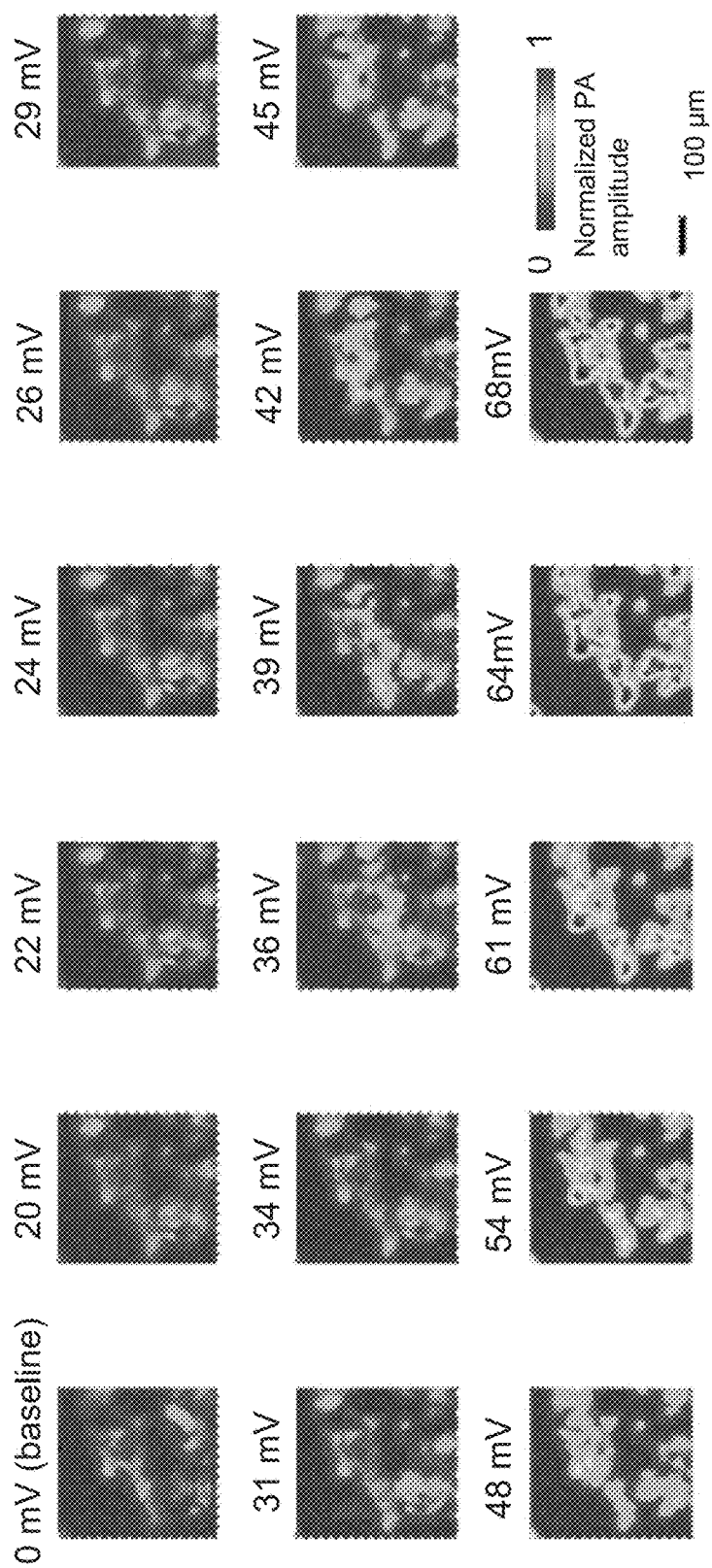
FIG. 3 is a series of PA images of HEK 293 cells stained with DPA obtained at different membrane resting potentials relative to a 0 mV baseline: 0 mV, 20 mV, 22 mV, 24 mV, 26 mV, 29 mV, 31 mV, 34 mV, 36 mV, 39 mV, 42 mV 45 mV, 48 mV, 54 mV, 61 mV, 64 mV and 68 mV.

Example 3: Our Preliminary Results Demonstrate PA Contrast in Imaging the Cell Membrane Action Potential with DPA Alone We conducted preliminary experiments again with HEK 293 cell culture preparation and a transmission mode optical resolution photoacoustic microscope, except that HEK 293 cells were stained only with DPA [1]. Similarly, we first imaged stained cells in DPBS using OR-PAM to acquire a baseline image. Then we changed the cell membrane resting potential by varying the cell's external environmental potassium ($K^+$) concentration. FIG. 3 shows a series of PA images of HEK 293 cells under different membrane resting potentials.

Figure 4:
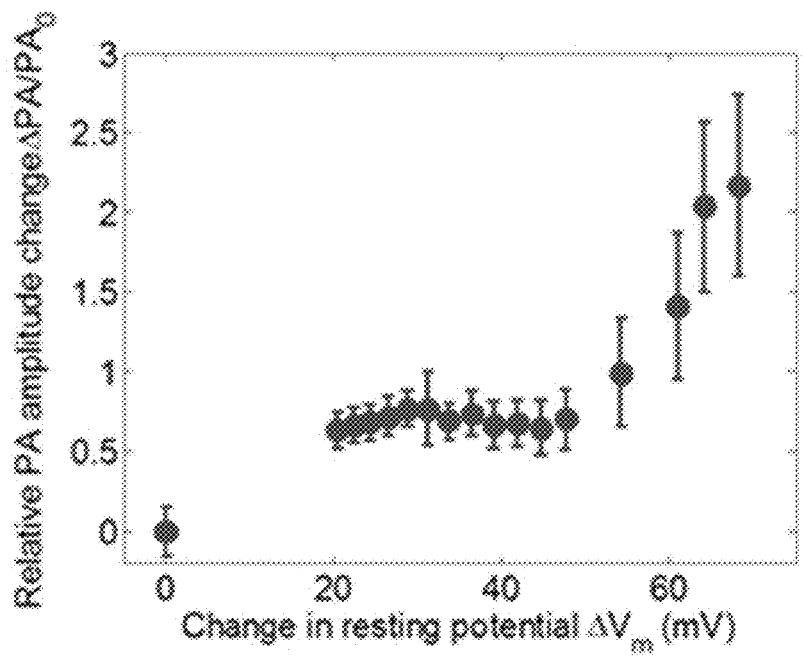
FIG. 4 is a graph of PA amplitude changes at different resting potentials relative to the baseline PA amplitude $PA_0$ measured at a baseline membrane potential $V_{m0}$.

FIG. 4 shows the PA amplitude of HEK 293 cells normalized to PA amplitude at $V_{m0}$ under different relative resting potentials, calculated from the chosen areas of cells denoted by red dashed squares in FIG. 3. The error bar represents one standard deviation. Our results clearly demonstrate that we have discovered an innovative voltage-sensitive photoacoustic imaging probe. We observed a ~200% increase in PA signal with a ~68 mV membrane resting potential change induced by altering the potassium ($K^+$) concentration in the extracellular space.

Figure 5:
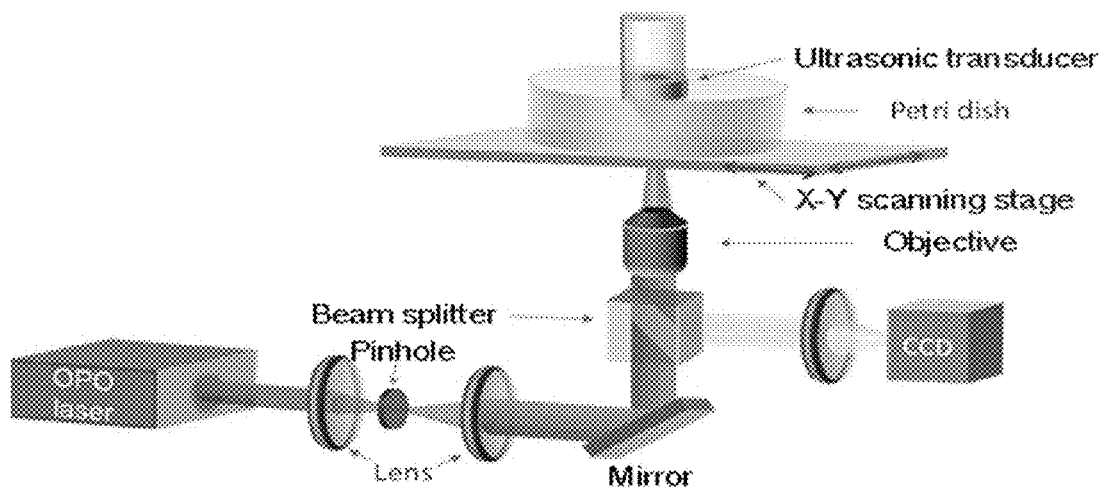
FIG. 5 is a schematic diagram illustrated an OR-PAM neuroimaging system according to one aspect.

Example 4: Simultaneous OR-PAM and Voltage Clamp Recording of the Membrane Potentials A voltage clamp system was integrated into a transmission-mode optical-resolution photoacoustic microscope (OR-PAM) (FIG. 5). HEK 293 cell membrane potential will be clamped and simultaneously measured by both OR-PAM.

A stereo microscope (not shown in FIG. 5) will be used to set up the voltage clamp on a single HEK 293 cell. We will also use the stereo microscope to align the clamped cell's center with the OPO excitation laser beam. The acoustic transducer can be translated or rotated in or out of the optical train by a mechanical switch or rotator (not shown in FIG. 5). We will use a 2 kHz laser (IS400-3-L, Edgewave and Credo-DYE-N, Newport) tunable from 400 to 920 nm, which gives a time resolution of 0.5 ms. With cells clamped at different membrane voltages, responses will be imaged by OR-PAM.

Example 5: Optimize the Laser Wavelength and Laser Pulse Energy for the Voltage-Sensitive Photoacoustic Imaging Probe We will use the experimental setup in FIG. 5 to optimize the laser excitation wavelength (350 nm to 550 nm) for best detection sensitivity. We can also observe the effects of different laser pulse energy. Collectively, we can adopt the best strategy to sense changes in the cell membrane voltage.

Example 6: Search for Longer Wavelength Voltage-Sensitive Photoacoustic Imaging Probes To minimize optical attenuation in tissue, we will screen various voltage-sensitive dyes for photoacoustic imaging at a longer wavelength (red or NIR). Historically, three main classes (merocyanines, cyanines, and oxonols) of polymethine dyes have been used to sense action potential. Recently, photoacoustic imaging technologies have been invented for biomedical applications. Most of the above dyes have not been tested with photoacoustic imaging technologies. An initial list of commercially available voltage-sensitive dyes to be tested for PA imaging along with their peak absorption wavelengths are shown in Table 1. The procedures described in Examples 4 and 5 will be repeated for each candidate in the list. Further screening of other dyes will be considered as well.

TABLE 1

| | | | | | Potential voltage-sensitive dyes for photoacoustic imaging. Abs.: peak absorption wavelength | | | | | | |
|---|---|---|---|---|---|---|---|---|---|---|---|
| Dye | NK 2761 | RH 155 | RH 482 | RH 1691 | RH 1692 | RH 1838 | RH 414 | RH 795 | RH 160 | RH 237 | Di-12-ANEPPQ | Di-2-ANEPEQ |
| Abs. (nm) | 716 | 700 | 670 | 630 | 630 | 630 | 532 | 530 | 530 | 528 | 519 | 517 |

Figure 6:
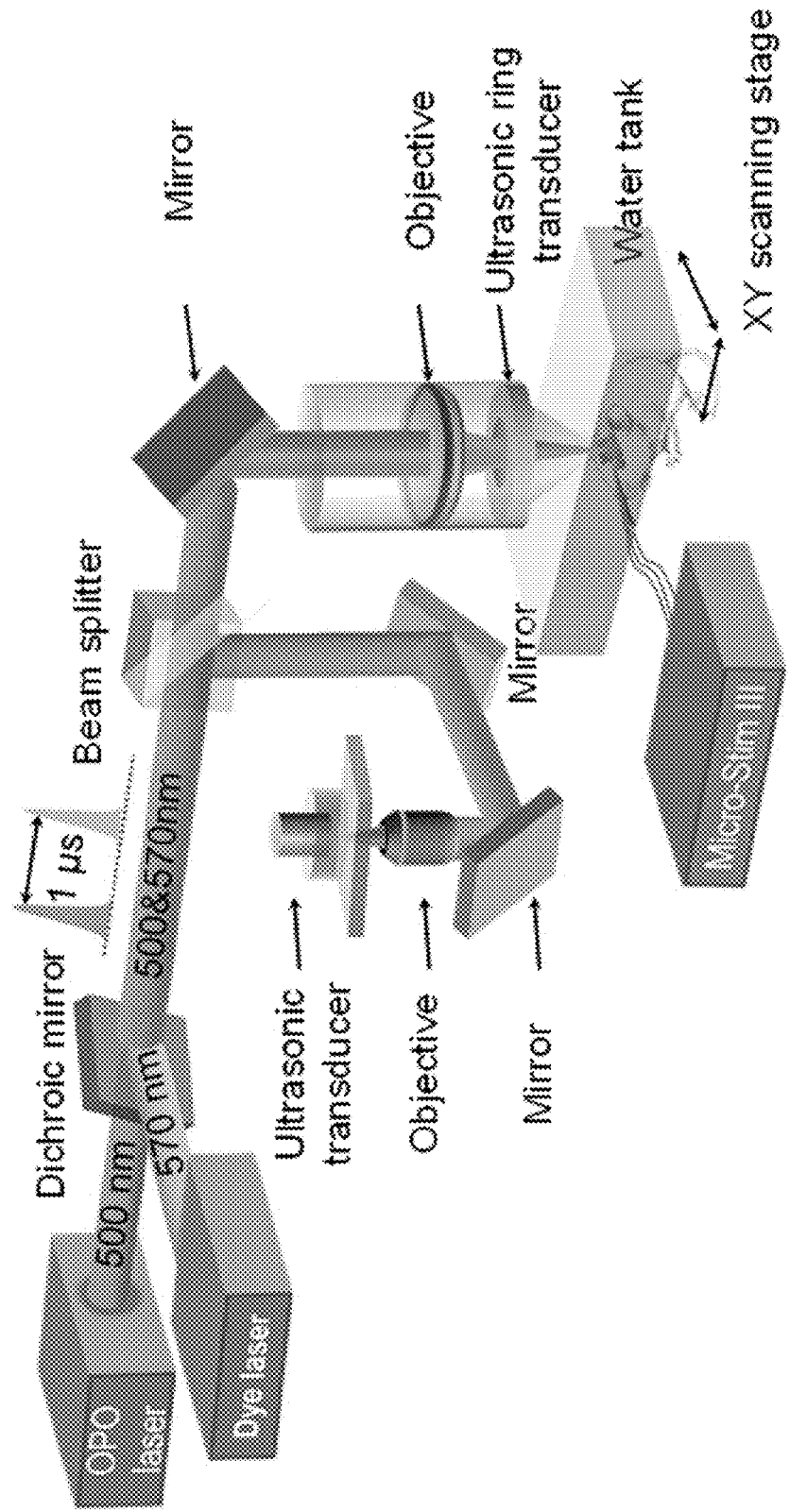
FIG. 6 is a schematic diagram of a photoacoustic neuroimaging system based on a full-ring transducer array according to one aspect.

Example 7: Develop a Fast, High-Resolution, Deep-Penetration Photoacoustic Computed Tomography System A diagram of the proposed PACT system is shown in FIG. 6. To ensure high spatial resolution in deep brain imaging, we propose to use high frequency (20 MHz) ultrasound transducer arrays: a ring-shaped one and a linear-shaped one. The photoacoustic signal will be amplified and digitized by four commercial ultrasound acquisition systems (SonixDAQ, Ultrasonix Inc.) (FIG. 6). Compared with the custom-built data acquisition system in our prototype, the Ultrasonix systems have several advantages: (a) more parallel data acquisition channels (512 vs. 64) are provided; (b) each channel is equipped with a large buffer memory (capable of storing 32000 frames), allowing continuous sampling over a long duration without transferring data to computer memory; and (c) the system has a two times higher sampling rate (80 MHz), sufficient for acquiring data from 20 MHz transducer arrays.

To ensure capturing fast neural dynamics, we will employ a 2 kHz pulsed laser system (IS400-3-L, Edgewave and Credo-DYE-N, Newport) tunable from 400 to 920 nm, which will be able to cover the excitation wavelength of the selected voltage-sensitive dye. With the matched number of data acquisition channels and array elements, photoacoustic tomography can be performed at 2 kHz, providing 2D cross-sectional imaging faster than any existing PACT systems. Our prototype and the proposed ring-shaped system are compared in Table 2.

array will also be mechanically shaped to produce an axial focal depth of 47.5 mm. The combined foci of all elements will form a 15-mm-diameter imaging region in the ring center. Within this region, the axial (radial) resolution will be 25 µm, and the transverse (tangential) resolution will vary between 25 µm and 72 µm (based on theoretical estimation). Using the focal-line image reconstruction algorithm, the elevational (z-axis) resolution will be 427.5 µm throughout the field of view. This slice thickness and diameter will enable tomography for an entire small animal brain, with selectivity in depth.

A metal cylinder will be installed in the array housing as shown in FIG. 7, and the bottom of the cylinder will be sealed with a rubber film. The array will be connected to the four Ultrasonix systems via custom-made multi-coaxial ultrasound cables (FIG. 6).

Figures 7A, 7B:
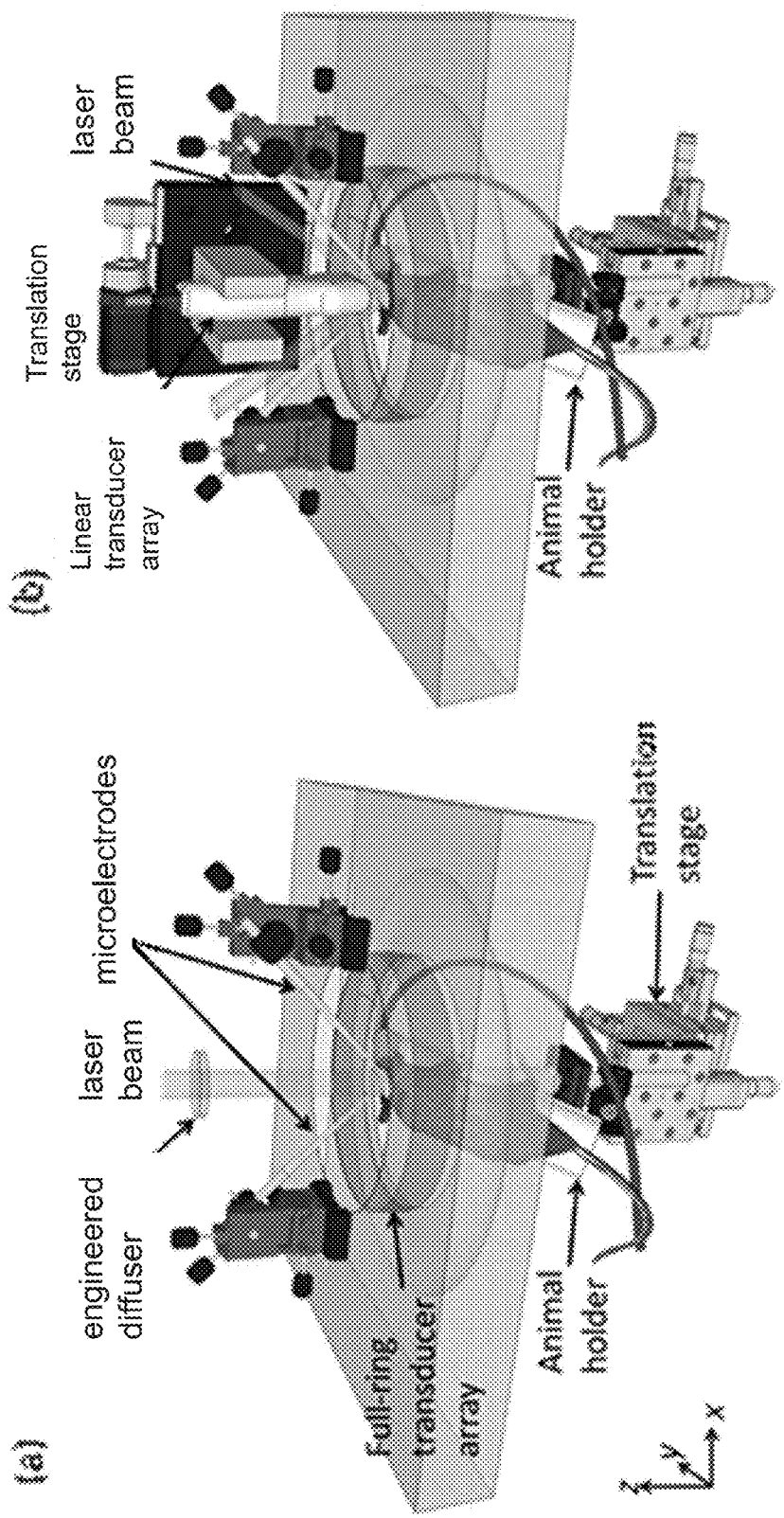
FIG. 7A is a perspective drawing of a photoacoustic neuroimaging system based on a full-ring transducer array according to one aspect.
FIG. 7B is a perspective drawing of a photoacoustic neuroimaging system based on linear transducer array according to one aspect.

We will also employ a 20 MHz linear transducer array (FIG. 7(b)) to image the brain from above. Compared to the full-ring array, the linear array allows imaging the brain dynamics in coronal or sagittal views. As will be illustrated in the following section, the top skull can be thinned or completely removed, and thus the coronal- or sagittal-view brain images will have minimum acoustic distortion from the skull. Besides high-speed dynamic imaging, we can also linearly scan or rotate the linear array within the x-y plane to acquire three-dimensional (3D) structural or vascular images, with an axial (z axis) resolution of 25 µm. The combination of full-ring and linear arrays will provide high-resolution imaging of the brain along all three axes.

TABLE 2

Comparison of prototype and proposed ring-shaped photoacoustic neuroimaging systems.

| | Central frequency | Ring diameter | No. of elements | DAQ channels | Imaging speed | Dynamic range | Spatial resolution | Pulse repetition rate |
|---|---|---|---|---|---|---|---|---|
| Prototype | 5 MHz | 5 cm | 512 | 64 | 0.625 fps | 10 bits | 100 µm | 10 Hz |
| Proposed | 20 MHz | 10 cm | 512 | 512 | 2000 fps | Up to 12 bits | 25 µm | 2 kHz |

Example 8: Ultrasonic Detection

The full-ring ultrasonic transducer arrays will be 10 cm in diameter and equipped with 512 elements (Imasonic). The central frequency of 20 MHz will provide high spatial resolution (~25 µm) in deep (~10 mm) tissues. Compared with commercially available high-frequency linear transducer arrays, our full-ring design has full acoustic coverage within the imaging plane, which is essential for photoacoustic imaging.

The height and width of each array element will be 10 mm and 0.075 mm (one acoustic wavelength at 20 MHz), respectively, leading to a pitch of 0.307 mm and an inter-element distance of 0.232 mm. Each element in the focused Example 9: Light Delivery We will mainly use planar top illumination (FIG. 7(a)). The laser beam, homogenized by an engineered diffuser, will illuminate the mouse brain directly from above. With the linear array addition, the laser beam will be split into two using a fiber optical bundle and will illuminate from both sides (FIG. 7(b)).

Example 10: Animal Mounting

Before the experiment, the full-ring array will be sealed in the bottom with a transparent membrane and filled up with water. The animal will be mounted on a lab-made holder, consisting of a metal plate for supporting the animal body and a mask for breathing (FIG. 6 and FIG. 7A and FIG. 7B). The holder will also be equipped with a tooth bar to prevent head movement and a heating pad to maintain the body temperature. The animal will then be held in an upright position with the brain covered by the transparent membrane. Ultrasound gel will be used to ensure good acoustic coupling between the membrane and the mouse head. The position of the animal can be adjusted through a three-dimensional translation stage. The temperature in the water tank will be maintained at 36° C. by another heating pad placed on the transducer housing. The constant temperature will ensure both animal comfort and a stable speed of sound for accurate imaging reconstruction.

Example 11: Craniectomy or Skull Thinning

For deep brain imaging, to reduce acoustic wave attenuation and aberration by the skull, we will perform craniectomy or skull thinning. Craniectomy, involves permanent removal of a portion of the mouse skull. Top skull will be removed (FIG. 8(a)) for linear-array-based top detection. Skull thinning is another possible procedure to reduce the acoustic distortion. Compared to craniectomy, a larger portion of the skull can be thinned without harming the animal. For the full-ring transducer array detection, the parietal area of the skull will be thinned (FIG. 8(b)). Such procedures have been routinely performed by our Animal Surgeon, Ernesto Gonzales.

Example 12: Feasibility

Over the past few years, we have developed multiple photoacoustic imaging systems with different spatial resolutions and penetration depths. For deep brain imaging, we constructed acoustic-resolution photoacoustic microscopy (AR-PAM) and ring-shaped photoacoustic computed tomography (PACT) systems, which can image through the intact scalp with 30-100 µm spatial resolutions. FIG. 9A is an in vivo image of a mouse brain cortex acquired noninvasively using the prototype 5-MHz full-ring array PACT system. The spatial resolution of the system is ~100 µm within the brain cortex. Rich vascular structures of the brain cortex can be clearly seen in the image. In comparison, a photograph of the brain with intact scalp does not show any cortical vessels (FIG. 9B). The mouse was then euthanized and the scalp was removed. The open-scalp photograph (FIG. 9C) agrees well with the photoacoustic image in FIG. 9A, indicating that PACT can image cortical vessels through intact scalp and skull. We also invented optical-resolution photoacoustic microscopy (OR-PAM) for high resolution brain imaging. FIG. 9D is an OR-PAM image acquired through the exposed skull. With 2.1 µm spatial resolution, the OR-PAM system can resolve cortical microvasculature at single capillary levels.

Figure 10A:
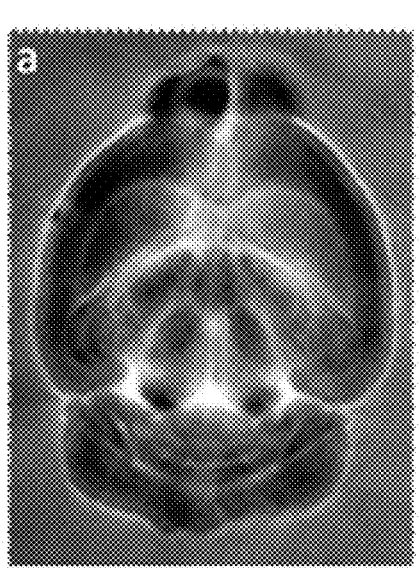
FIG. 10A is a photoacoustic image of an excised mouse brain perfused with saline obtained at a depth of 2.4 mm acquired using a full-ring array PACT system at 610 nm wavelength according to one aspect.
Figure 10B:
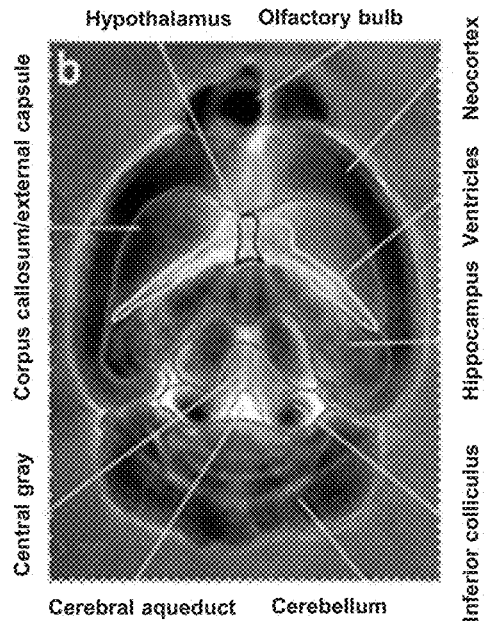
FIG. 10B is the image of FIG. 10A with labeled brain structures.
Figure 10C:
FIG. 10C is photoacoustic image of an excised mouse brain without saline perfusion obtained at a depth of 2.4 mm acquired using a full-ring array PACT system at 610 nm wavelength according to one aspect.
Figure 10D:
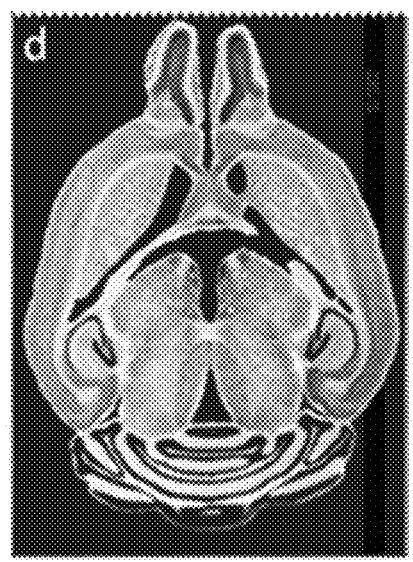
FIG. 10D is a mouse brain image acquired by histology obtained from the literature.
Figures 11A, 11B, 11C, 11D:
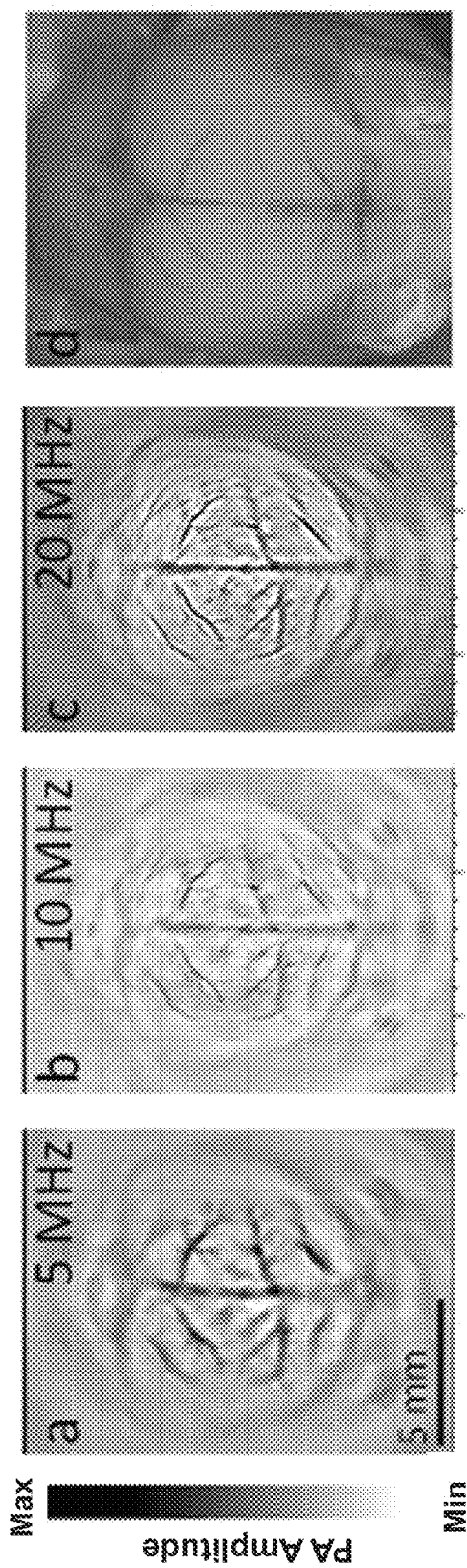
FIG. 11A is a photoacoustic image of a mouse brain acquired using a PACT system with a 3.5 MHz transducer.
FIG. 11B is a photoacoustic image of a mouse brain acquired using a PACT system with a 10 MHz transducer.
FIG. 11C is a photoacoustic image of a mouse brain acquired using a PACT system with a 20 MHz transducer.
FIG. 11D is a top-view photograph of the mouse brain with the scalp was stripped away after the photoacoustic imaging.

The prototype full-ring array PACT system can also be used to image deep brain structures. FIG. 10A an image of an excised mouse brain perfused with saline. Different brain structures can be clearly identified, including central gray, cerebellum, cerebral aqueduct, corpus callosum, hippocampus, hypothalamus, inferior colliculus, neocortex, olfactory bulb, and ventricles (FIG. 10B). We also imaged a brain without saline perfusion. Some of the brain structures, such as the olfactory bulb, neocortex, corpus callosum, hippocampus, and cerebellum can still be identified. These results indicate that PACT has rich contrast among different brain tissues, and once the skull distortion can be minimized, PACT can provide high resolution structural and vascular images of the brain. It is for the first time that PACT shows x-ray CT like images.

We have also validated the feasibility of noninvasively imaging the mouse brain with high frequency ultrasound transducers. In that study, we used three single-element ultrasound transducers, each with a different central frequency, to simultaneously scan around an adult BALB/c mouse brain. The results, shown in FIG. 11A, FIG. 11B, FIG. 11C, and FIG. 11D, clearly indicate that the higher frequency detectors provided finer image resolution. The spatial resolutions were quantified to be 210 µm, 60 µm, and 30 µm for the three transducers, respectively. Our proposed high frequency transducer array, with a wider bandwidth, can potentially achieve even better spatial resolution (25 µm). As all images were acquired through the intact scalp, our results also indicate that a 20 MHz high frequency transducer can effectively image through the mouse skull, which will be removed or thinned to reduce loss further.

Depending on the excitation wavelength of the chosen dye, it is possible that, in top illumination, the light may not penetrate through the entire brain. In this case, we will try different light illumination schemes, such as internal light delivery through the mouth using a side-firing optical fiber or side illumination using ring-shaped light. For deep brain imaging using the full-ring transducer array, the nasal and the ear cavities may distort the acoustic signal. As the location of these cavities may be estimated based on a brain atlas or imaged using X-ray CT or MRI, we may use advanced image reconstruction algorithms to mitigate the distortion.

Example 13: Use PACT to Image Action Potentials in the Brain of Small Animals In Vivo, Surgical Procedures and Dye Staining 3-month-old C57bl6 male mice will be anesthetized with isoflurane via face mask (2.0% induction, 1.0% maintenance; flow rate of 1.0 L/min.), and placed on a custom stereotaxic imaging stage. The left dorsal portion of the skull will be exposed by removing the scalp and temporal muscle. Using a dental drill, a cranial opening will be made over the left somatosensory cortex, and the exposed dura matter surface will be cleaned with artificial cerebrospinal fluid. Voltage-sensitive dye dissolved in DMSO will be pressure-ejected over a 15 min period into the hippocampus with a quartz pipette (5 to 10 µm opening), using stereotaxy (0.9 mm lateral, 1.8 mm posterior to bregma; and depths of 1.8 mm from the brain surface to reach the dentate gyrus, and 1.6 mm to reach CA1 and CA3). The dye will be injected bilaterally. The well, created by the craniotomy, will be filled with 1.5% agarose in 0.9% NaCl and coverslipped. Adequate time will be given to allow the dye to spread evenly. Immediately after this procedure, the mouse will be imaged by PACT with isoflurane anesthesia. Throughout the skull preparation and imaging, the mouse will be maintained at 37° C. using a temperature-controlled heating pad. After imaging, postmortem histology will be performed to ensure no damage is caused by the skull preparation and injection and to confirm electrode placement.

Example 14: Electrical Stimulation, PACT Imaging and Local Field Potential Recording We will induce neuronal activity in the hippocampus (to be imaged with the PACT) using electrical stimulation of the perforant pathway. The hippocampus is targeted for imaging to demonstrate the deep-penetration ability of our improved PACT system, imaging prior to and after electrical stimulation. Local field potential will be recorded to verify the action potentials measured by PACT at three different locations within the hippocampus (dentate gyrus, CA1, and CA3). Local field potential recordings will be obtained with a DP311 pre-amplifier (Warner Instruments), and digitized at 10 kHz using PCIe-6321 DAQ, (National Instrument).

To induce neuronal activity in the hippocampus, we will stimulate the angular bundle of the perforant pathway. A bipolar stimulation electrode (NE-200, 0.5 mm tip separation, Rhodes Medical Instruments, USA) will be introduced into the angular bundle at 2.1 mm lateral and 3.8 mm posterior to Bregma and lowered to a depth of 1.6 mm from the brain surface. Individual stimulation pulses (pulse amplitude 100-5000 pA; pulse duration: 0.2 ms; repetition rate: 0.1 Hz) will be generated by a stimulator (A365; World Precision Instruments, Sarasota, Fla.) triggered by a function generator (DS345; Stanford Research Systems, Sunnyvale, Calif.). An input-output curve for the population spike amplitude will be obtained for each animal, and the stimulus intensity adjusted to half-maximal amplitude to correlate with PACT imaging. Cross-sectional PACT images of the mouse brain will be captured at a frame rate of 2 kHz. The electrical stimulation will induce the firing of action potentials, and will result in an increase in PA signals as demonstrated in Aim 1. To reduce noise, PACT images will be averaged over 10 trials at each location, with 35 s interval between trials. After averaging, the change in PA signal will be calculated. To confirm the specificity of stimulation-evoked PA signals with that of electrophysiological measurements, Tungsten recording electrodes (TM33A10KT, World Precision Instruments, USA) will be placed in the dentate gyrus (AP-2.0, ML 1.6, DV-2.0), and simultaneous imaging of PACT and electrophysiological recordings will be performed. After the 10 trials, the recording electrode will be removed, and then replaced into CA1 (AP-1.6, ML 1.0, DV-1.5); and additional recordings will be performed (10 trials). Finally, the electrode will be removed and replaced into CA3 (AP 1.6, ML 2.5, DV-1.5) for the final set of recordings. Imaging will be performed on three groups (each group for one hippocampal location), with five mice in each group. All animal protocols and procedures will follow the guidelines approved by the Washington University School of Medicine Animal Care and Use Committee.

Example 15: Cross-Correlation Analysis

To validate the PA signal change from the voltage-sensitive dye, cross-correlation analysis will be performed between the PA signals and the local field potential recordings. At each depth, the electric stimulation, PACT imaging and the local field potential recording will be performed simultaneously at three different locations. At each location, the temporal correlations between local field potential and PA will be calculated respectively. For the temporal correlation, the time-dependent stimulus-evoked changes of PA signals will be calculated as $\Delta PA/PA_0=(PA(t)-PA_0)-PA_0$. $PA_0$ is the PA signal averaged over several pixels in the PACT image before the stimulation onset. PA(t) is the PA signal averaged over the same area at a given time t after the stimulation. Cross-correlations will be performed between the fractional PA signals $\Delta PA_0/PA_0$ and the local field recording signals $\Delta P/P_0$, which is:

$$CC(\Delta t) = \sum_t (\Delta PA/PA_0)(t) \cdot (\Delta P/P_0)(t - \Delta t) \quad (1)$$

Data analysis will be performed with MatLab. Statistical analysis will be performed for data from different groups of mice.

Example 16: Anticipated Problems and Solutions

The perforant pathway connects to the DG via a monosynaptic connection; however, CA1 and CA3 connect with the perforant pathway via a polysynaptic connection. Therefore, the field potential signals in CA1 and CA3 might not be consistently coupled to perforant path stimulation. Because we are interested in the correlation between PA signals and electrophysiological signals (via the wire electrode), this inconsistent coupling is not an issue, and will in fact be a better test the correlation. It is possible that this inconsistent coupling could result in a loss of signal. In such a case, the stimulation parameters, such as the amplitudes and frequency of the stimulus pulse will be adjusted to optimize the field potential signals for the correlation. In the temporal correlation, the chosen pixels in the PACT image may not be optimal for the correlation calculation and can thus be adjusted.

The above cross-correlation model assumes a linear relationship between the fractional PA signal change and the membrane potential change. Depending on the choice of dye, the relationship may be exponential or other mathematical forms. The corresponding fractional PA signal change should be calibrated before correlating with the field recording signals.

Example 17: Feasibility

Figures 12A, 12B:
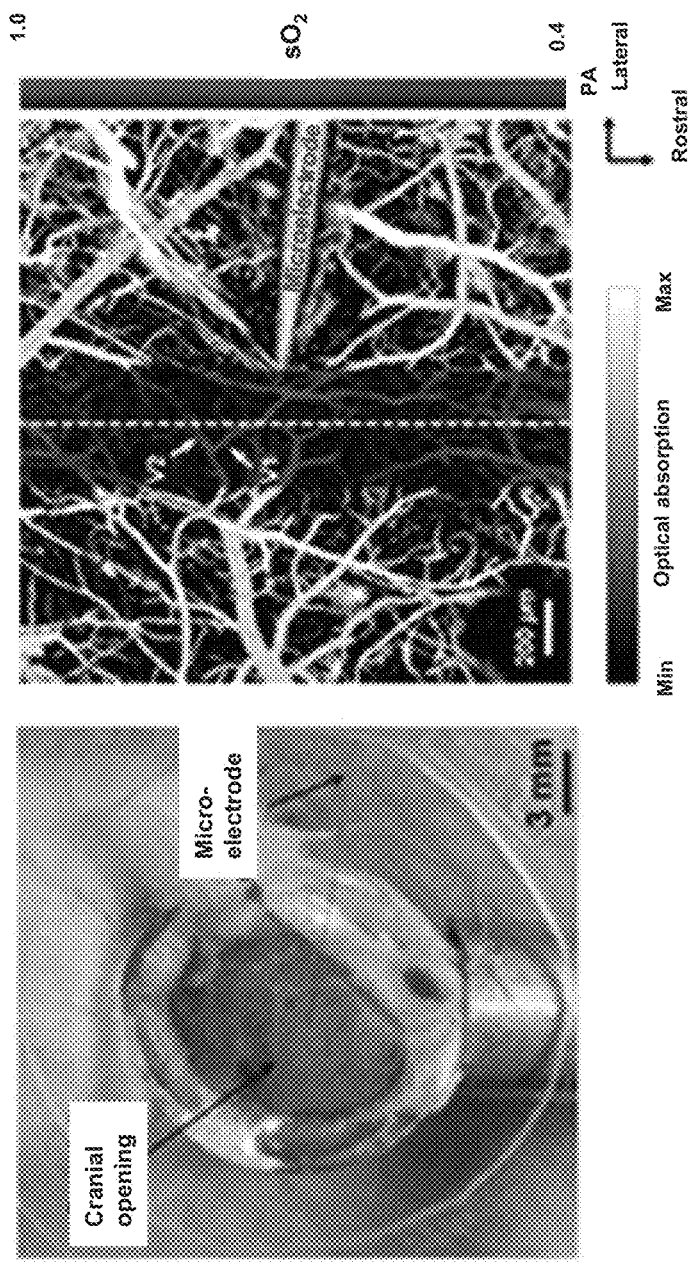
FIG. 12A is a photograph of an exposed brain surface with an introduced microelectrode.
FIG. 12B are superimposed open-skull photoacoustic images of the mouse cortical microvasculature.

Our group has extensive experience in multi-scale and multi-depth brain imaging. Using the OR-PAM system, we successfully imaged the vascular response to cortical electrical stimulation at the microscopic level [32]. Following the same animal preparation procedure described herein using two wavelengths (570 and 578 nm) to quantify the oxygen saturation of hemoglobin (sO2) within a small region of interest around the tip of the microelectrode (FIG. 12(a) and FIG. 12(b)). The high spatial resolution of OR-PAM enables the analysis of single microvessel responses to cortical electrical stimulation.

Figure 13:
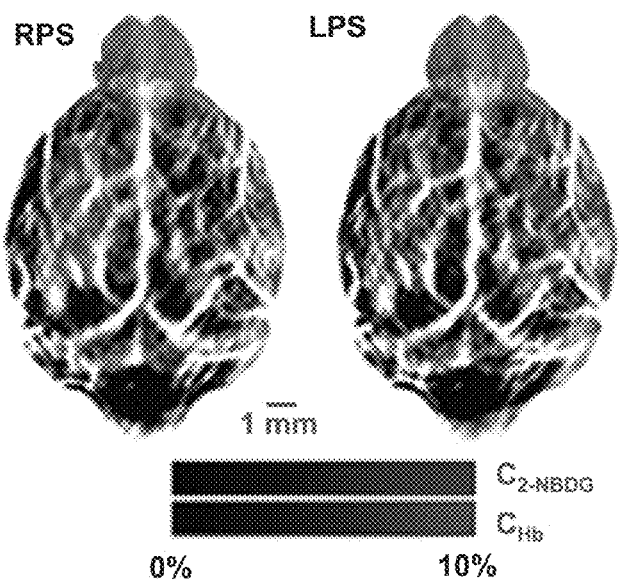
FIG. 13 is a pair of overlaid photoacoustic images showing the relative changes of 2-NBDG concentration ($C_{2-NBDG}$, shown in blue) and total hemoglobin concentration ($C_{Hb}$, shown in red), superimposed on the vascular photoacoustic image obtained at 570 nm (shown in gray) in response to right paw stimulation (RPS) and left paw stimulation (LPS).
Figures 14A, 14B:
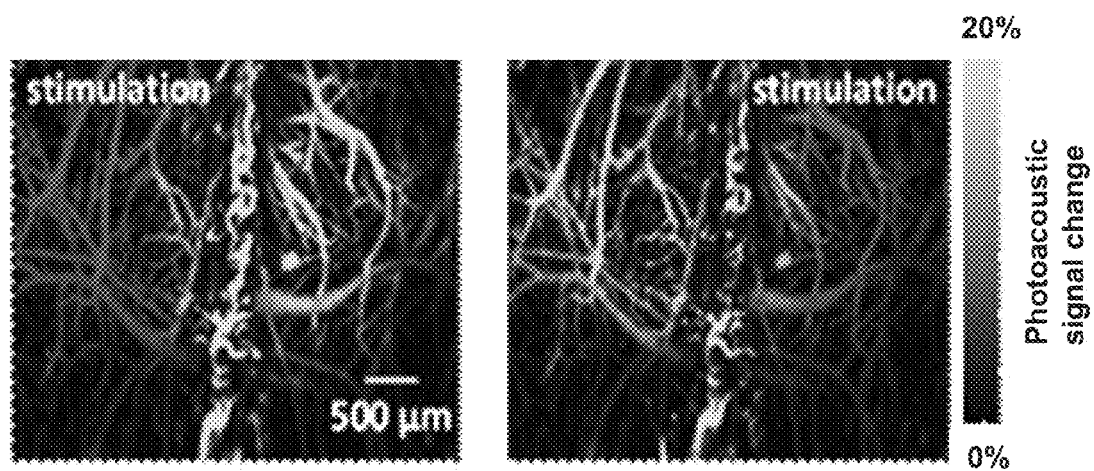
FIG. 14A is a photoacoustic microscopic image of a mouse brain showing relative photoacoustic amplitude changes in response to left hindlimb stimulation.
FIG. 14B is a photoacoustic microscopic image of a mouse brain showing relative photoacoustic amplitude changes in response to right hindlimb stimulation. For both images, the relative photoacoustic amplitude changes (yellow) were superimposed on the structural image (red).

Using a MEMS-mirror-based OR-PAM system, we can acquire microscopic images at 1 fps over a 3×4 mm2 region. The system was used to study the brain response to hindlimb stimulation. FIG. 13 shows the photoacoustic amplitude change overlaid on the structural image. A peak increase of 16% can be observed. The increase in photoacoustic signal amplitudes resulted from an increase in the total hemoglobin concentration in the resolution voxel, which reflected the elevated neural activity evoked by the stimulations.

Our prototype 5 MHz full-ring system has also been successfully used to acquire metabolic, functional, and dynamic images of mouse brains. The metabolic contrast was provided by a fluorescent 2-deoxyglucose analog—2NBDG, which enabled us to study the brain metabolic response to forepaw stimulation [33]. Two wavelengths were used in the study: 478 nm (the peak absorption wavelength for 2-NBDG) and 570 nm (the isosbestic wavelength for Hb and HbO2 absorption). Thirty minutes after tail-vein injection of 2-NBDG, the mouse was stimulated through needle electrodes inserted under the skin of the forepaws. Each paw received two 3 min stimulations, with a 3 min rest period between stimulations. As shown in FIG. 13, the stimulations caused an increase in both total hemoglobin concentration and glucose metabolism, indicating close coupling between oxygen metabolism and glucose metabolism in the brain.

Our prototype system has also been able to image the resting-state functional connectivity in the mouse brain. The experiment was performed non-invasively on 3-4 month old male Swiss Webster mice. Each mouse was imaged over a span of 10 minutes, yielding 360 image frames. To extract the resting-state signal, the reconstructed images were processed through spatial smoothing, mean pixel value subtraction, temporal filtering (to the functional connectivity frequency band), and global regression. A seed-based algorithm was then used to derive the functional connectivity maps. The results (FIG. 15A, FIG. 15B, and FIG. 15C) clearly indicate bilateral correlations in eight main regions, as well as several subregions. A unique advantage of PAT is that the functional connectivity maps are automatically co-registered with high-resolution cortical vascular images, allowing us to pinpoint the location of neural activity.

The imaging speed of our current prototype system is 0.625 fps, which is mainly limited by the custom-made data acquisition system. The 2000-fps imaging speed in the proposed new system will allow us to capture real-time action potentials, such as responses to stimulation. The improved spatial resolution will also provide better vascular, metabolic, and functional imaging of the brain, yielding a unique system for comprehensive neuroimaging.

Figures 16A, 16B, 16C:
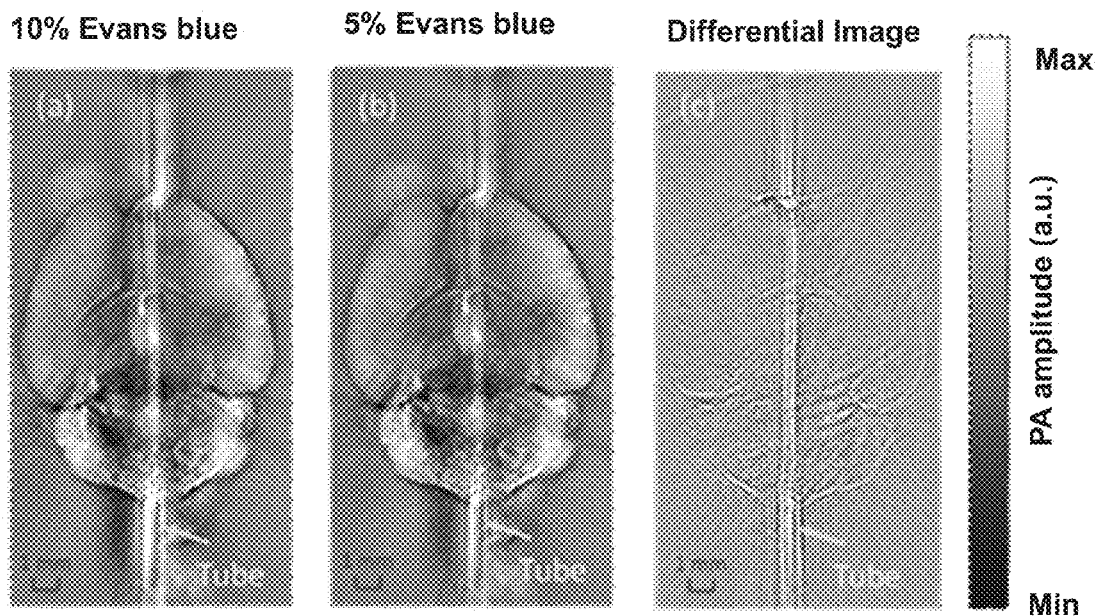
FIG. 16A is a PACT image of a tube with 10% Evan blue concentration placed at 3 mm depth in a mouse brain.
FIG. 16B is a PACT image of a tube with 5% Evan blue concentration placed at 3 mm depth in a mouse brain.
FIG. 16C is a differential image obtained from the PACT images of FIG. 16A and FIG. 16B.

Deep brain imaging capability was demonstrated by our prototype PACT system. We have differentially imaged a tube 3 mm deep below the mouse brain cortex ex vivo. In the experiment, a tube containing 10% and 5% Evans blue dye was inserted sequentially into a fixed mouse brain at 3 mm depth. Then the mouse brain was embedded in 3% agar gel. Two PACT images were taken at 610 nm with 10% and 5% Evans blue tubes, respectively, as shown FIG. 16A and FIG. 16B. A differential image from these two images as shown in FIG. 16(c) clearly shows the tube, which indicates the feasibility of differentially imaging the action potential deep in the mouse brain.

Figures 17A, 17B:
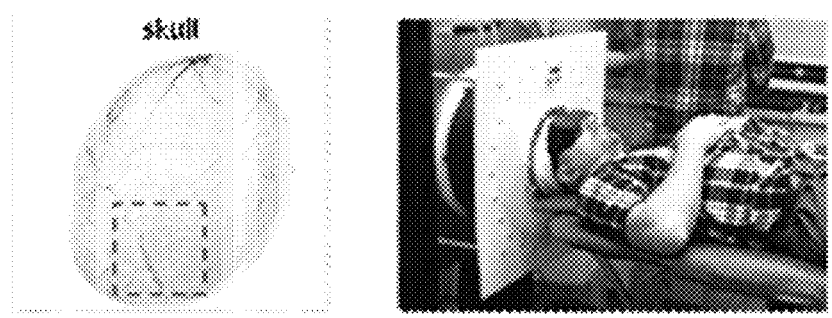
FIG. 17A is an MRI image of the scalp and skull of a healthy human subject.
FIG. 17B is a photograph of the PACT scanner during imaging of the brain of a healthy human subject.
Figures 17C, 17D:
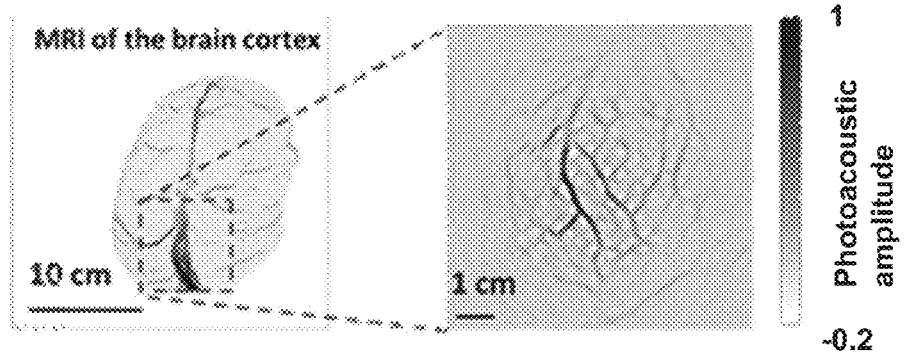
FIG. 17C is an MRI image of the brain cortex of a healthy human subject.
FIG. 17D is a PACT brain image of a healthy human subject.

Photoacoustics also has great potential for imaging the brains of larger animals or even humans. FIG. 17(d) is a preliminary unpublished photoacoustic brain image acquired on a healthy human subject in vivo with intact scalp. A 1 MHz transducer scanned circularly around the subject's head illuminated by laser light at a wavelength of 1064 nm. Several vessels can be clearly identified in the image. From the corresponding MRI image of the same human subject in FIG. 17(a) and FIG. 17(c), we can see more resemblance between MRI cortex image and the PACT image. While further investigation is still underway, it is most likely that these vessels in the PACT image come from the brain cortex instead of the scalp. This study indicates that PAT can potentially be used for functional brain imaging in humans.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of performing photoacoustic tomography of at least one electrically-active cell of a subject, the method comprising:
    contacting the at least one electrically-active cell within a target area with a voltage-responsive dye;
    illuminating the target area with a light pulse;
    detecting at least one photoacoustic signal produced by the voltage-responsive dye, wherein the voltage-responsive dye is selected from a merocyanine-rhodanine dye; an aminonaphthylethenylpyridinium dye including Di-4-ANEPPS, di-8-ANEPPS, Di-2-ANEPEQ, Di-8-ANEPPQ and Di-12-ANEPPQ, a dialkylaminophenylpolyenylpyridinium dye including RH 160, RH 237, RH 414, RH 421, and RH 795; an oxonol dye including RH 155, RH 482, RH 1691, RH 1692, and RH 1838; and dipicrylamine (DPA);
    comparing a time-of-arrival of the at least one photoacoustic signal to determine a position of the at least one electrically-active cell; and
    transforming at least one characteristic of each photoacoustic signal according to a calibration rule to determine a membrane voltage of the at least one electrically-active cell contacted with the voltage-responsive dye, the calibration rule comprising a relationship between the at least one characteristic of each photoacoustic signal and the membrane voltage of the at least one electrically-active cell, wherein the at least one characteristic is chosen from: amplitude, duration, temporal profile, frequency, and any combination thereof.

2. The method of claim 1, wherein the light pulse comprises a pulse wavelength corresponding to a maximum absorption wavelength of the voltage-responsive dye.

3. The method of claim 2, wherein the pulse wavelength ranges from 400 nm to 920 nm.

4. The method of claim 3, wherein the light pulse further comprises a pulse frequency of at least 1 kHz.

5. The method of claim 4, wherein the target area is illuminated using at least one illumination scheme chosen from:
    directing the light pulse through a diffuser to produce planar top Illumination;
    directing the light pulse through at least two optic fibers and through one or more diffusers to produce illumination from two or more directions;
    directing the light pulse through a side-firing optical fiber into an external cavity of a subject chosen from a mouth, a nasal cavity, an ear canal, a gastrointestinal tract, a urethra, or a vagina;
    directing the light pulse through an optical fiber implanted within the subject; and any combination thereof.

6. The method of claim 5, wherein the at least one electrically-active cell is chosen from at least one of: a brain neuron, a spinal neuron, a peripheral neuron, a sensory neuron, a voluntary muscle cell, a smooth muscle cell, a cardiac muscle cell, and any combination thereof.

7. The method of claim 6, wherein the at least one photoacoustic signal is detected at a depth up to 50 mm.

8. The method of claim 7, wherein the at least one photoacoustic signal is detected within a detection time of less than 5 µs.

9. The method of claim 8, wherein the position of the at least one electrically-active cell is detected with a spatial resolution of less than 100 μm.

10. The method of claim 9, wherein the position of the at least one electrically-active cell is detected with a spatial resolution of 25 μm.

11. The method of claim 10, wherein the voltage-responsive dye is contacted with the at least one electrically active cell within the target area using a contact method chosen from: intravenous injection; intramuscular injection; intraventricular injection; spinal tap; craniotomy with direct contact of dye to cortical surface of brain; or introduction of dye into a cell preparation containing the at least one electrically active cell.

12. The method of claim 11, further comprising electrically stimulating a region within the target area to induce an electrical response within the target area.

13. The method of claim 12, wherein a hippocampus of a brain is the target area and a perforant pathway is electrically stimulated to induce a response within the hippocampus.

14. The method of claim 11, further comprising stimulating a sensory neuron to induce a response within the target area comprising a brain.

15. The method of claim 14, wherein the sensory neuron is chosen from a visual neuron, an olfactory neuron, an auditory neuron, a taste neuron, a pressure-sensitive neuron, and a temperature sensitive neuron.

16. The method of claim 11, wherein the target area comprises a brain, and a cognitive task is used to induce electrical activity within the target area.

\* \* \* \* \*